United States Patent
Ziobro et al.

(10) Patent No.: US 11,094,419 B2
(45) Date of Patent: Aug. 17, 2021

(54) SENSOR FUSION OF PHYSIOLOGICAL AND MACHINE-INTERFACE FACTORS AS A BIOMETRIC

(71) Applicant: DURO HEALTH, LLC, Portland, OR (US)

(72) Inventors: Randy T. Ziobro, Portland, OR (US); Collin C. Beeson, Portland, OR (US)

(73) Assignee: DURO HEALTH, LLC, Portland, OR (US)

( * ) Notice: Subject to any disclaimer, the term of this patent is extended or adjusted under 35 U.S.C. 154(b) by 272 days.

(21) Appl. No.: 16/129,655

(22) Filed: Sep. 12, 2018

(65) Prior Publication Data

US 2019/0080802 A1 Mar. 14, 2019

Related U.S. Application Data

(60) Provisional application No. 62/557,646, filed on Sep. 12, 2017.

(51) Int. Cl.
*G16H 50/30* (2018.01)
*G16H 20/30* (2018.01)
(Continued)

(52) U.S. Cl.
CPC ............ *G16H 50/30* (2018.01); *B64D 43/00* (2013.01); *G16H 10/60* (2018.01); *G16H 20/30* (2018.01); *G16H 40/63* (2018.01)

(58) Field of Classification Search
CPC ........ G16H 50/30; G16H 20/30; G16H 10/60; G16H 40/63; B64D 43/00
(Continued)

(56) References Cited

U.S. PATENT DOCUMENTS 9,298,985 B2 * 3/2016 Krueger ............... G02B 27/017
9,870,726 B2 * 1/2018 Yajima ............... A63F 13/5255
(Continued)

FOREIGN PATENT DOCUMENTS

WO 9741775 A1 11/1997

OTHER PUBLICATIONS

SMARTBASE Athlete Date Management Software, Fusion Sport, Available at www.fusionsport.com/smartabase-athelete-data-management-software, Retrieved on May 6, 2019, 10 pages.

*Primary Examiner* — Michael Tomaszewski
*Assistant Examiner* — Rachael Sojin Stone
(74) *Attorney, Agent, or Firm* — Alleman Hall Creasman & Tuttle LLP

(57) ABSTRACT

A biometric computing system obtains, via an inertial sensor, time-based inertial measurement data with respect to a human subject located on-board an aircraft for each of a plurality of on-board sessions with one or more aircraft. The time-based inertial measurement data may be transformed for each on-board session to a common reference frame that is shared by the plurality of on-board sessions. The transformed data of the plurality of on-board sessions are combined to obtain a time-based inertial measurement profile for the human subject. The biometric computing system further obtains, via a range of motion sensor, force-based range of motion measurement data with respect to the human subject interacting with a physiological measurement device across a range of motion. The force-based range of motion measurement data is combined with the time-based inertial measurement profile for the human subject to obtain a combined measurement profile for the human subject.

17 Claims, 15 Drawing Sheets

(51) Int. Cl.
*G16H 10/60* (2018.01)
*B64D 43/00* (2006.01)
*G16H 40/63* (2018.01)

(58) Field of Classification Search
USPC ............................................................ 705/3
See application file for complete search history.

(56) References Cited

U.S. PATENT DOCUMENTS

| | | | |
|---|---|---|---|
| 9,984,586 B2* | 5/2018 | Popa-Simil | G09B 9/085 |
| 10,642,270 B2* | 5/2020 | Duda | B64D 43/00 |
| 2002/0069089 A1 | 6/2002 | Larkin et al. | |
| 2002/0092350 A1* | 7/2002 | Etkin | G01V 7/16 |
| | | | 73/382 G |
| 2005/0108055 A1 | 5/2005 | Ott et al. | |
| 2006/0206027 A1 | 9/2006 | Malone | |
| 2006/0287879 A1 | 12/2006 | Malone | |
| 2009/0281879 A1 | 11/2009 | Pandya | |
| 2011/0077977 A1 | 3/2011 | Collins et al. | |
| 2014/0152792 A1* | 6/2014 | Krueger | G06K 9/00604 |
| | | | 348/78 |
| 2014/0212847 A1* | 7/2014 | Holder | G09B 19/165 |
| | | | 434/35 |
| 2016/0098808 A1 | 4/2016 | Ziobro | |
| 2018/0081439 A1* | 3/2018 | Daniels | G06F 3/015 |
| 2018/0349790 A1* | 12/2018 | Cai | G06N 20/00 |
| 2019/0154723 A1* | 5/2019 | Kacyvenski | G01L 1/00 |

* cited by examiner

SENSOR FUSION OF PHYSIOLOGICAL AND MACHINE-INTERFACE FACTORS AS A BIOMETRIC

CROSS REFERENCE TO RELATED APPLICATIONS

This application claims priority to U.S. provisional application 62/557,646, filed Sep. 12, 2017, the entirety of which is hereby incorporated herein by reference for all purposes.

BACKGROUND

Human operators of machinery and more specifically vehicles such as aircraft, for example, may experience acceleration events well beyond those otherwise experienced in the absence of machine interaction. Military pilots, for example, can experience acceleration events in excess of a gravitational force (g-force) measurement of 9 g. Acceleration events may be of prolonged duration, and specific types of acceleration events may be frequently and repeatedly encountered by human operators. Acceleration events may be described and quantified in terms of their directionality, magnitude, duration, and quantity with respect to a human subject.

SUMMARY

According to an aspect of the present disclosure, a biometric computing system obtains, via the one or more inertial sensors, time-based inertial measurement data with respect to a human subject located on-board an aircraft for each of a plurality of on-board sessions of the human subject with one or more aircraft. The biometric computing system stores the time-based inertial measurement data in a database system of the data storage subsystem in association with an identifier of the human subject and an identifier of a type of the aircraft for each of the plurality of on-board sessions. The biometric computing system selectively transforms the time-based inertial measurement data for each on-board session from a session-specific reference frame in multi-dimensional space to a common reference frame in multi-dimensional space that is shared by the plurality of on-board sessions. The biometric computing system combines the transformed time-based inertial measurement data for each on-board session of the plurality of on-board sessions to obtain a time-based inertial measurement profile for the human subject.

The biometric computing system further obtains, via the one or more range of motion sensors, force-based range of motion measurement data with respect to the human subject interacting with an instance of a physiological measurement device across a range of motion. The biometric computing system stores the force-based range of motion measurement data in the database system in association with the identifier of the human subject, and combines the force-based range of motion measurement data with the time-based inertial measurement profile for the human subject to obtain a combined measurement profile for the human subject. The biometric computing system stores the combined measurement profile in the database system in association with the identifier of the human subject, and outputs the combined measurement profile with the identifier of the human subject via a user interface of the computing system.

It will be understood that the above summary is provided to describe an example of the subject matter described in further detail by the detailed description and associated drawings, and that this example should not be interpreted as limiting the scope of the claims.

DETAILED DESCRIPTION

Military pilots have specialized job requirements that are unique to their profession. The high speed and high performance of fighter jet aircraft can exact a physical toll on those pilots that fly them. This physical toll can manifest as general injuries and ailments of a pilot and as military pilot-specific injuries caused by the unique demands of flying jet fighter aircraft.

The unique physical demands on the pilot can require a customized and/or specific fitness assessment and fitness improvement system/methods in order to accurately address these demands. Additionally, the workplace injuries incurred by pilots are very different than those of other professions and the potentially negative impact those injuries have on job performance are much greater. As such, there is a need for a fitness system and/or methods to address the specific needs of pilots and their fitness.

A pilot's individual fitness can prevent injuries, minimize the impact of injuries and/or reduce the recovery time of the pilot. The reduced injury rate and recovery time of a pilot is advantageous since it can increase pilot and unit readiness. As military pilots are highly trained specialists, the investment of time and financial resources in a military pilot are large. This results in a limited pool of qualified pilots and this pool can be stressed by injuries incurred by the pilots which further reduce the number pilots available for missions.

The disclosed pilot fitness systems and methods offer improved pilot fitness assessment, tracking and evaluation. The pilot fitness systems and methods allow for a wide range of assessment criteria, including the pilot and their fitness performance and their duty requirements, to be considered when evaluating the pilot and their fitness. Additionally, the pilot fitness systems and methods are iterative with repetitive assessment and evaluation to achieve desired fitness goals. This iterative process of assessment and evaluation can be performed with the use of a therapy or other device that can use machine learning to assist with the process. Previously, fitness assessment/evaluation and fitness planning were separate systems/processes, whereas the techniques disclosed herein provide a comprehensive and encompassing system and process that allow for individual pilot specific fitness evaluation, fitness improvement and injury treatment plans. Additionally, the pilot fitness systems and methods described herein allow for the early identification of pilot injury, including identification of pilot injuries the pilot themselves may be unaware of. The pilot fitness systems and methods can assist with maximizing pilot performance and readiness and provide a standardized assessment method that can be used in selecting pilots for missions.

Figure 1:
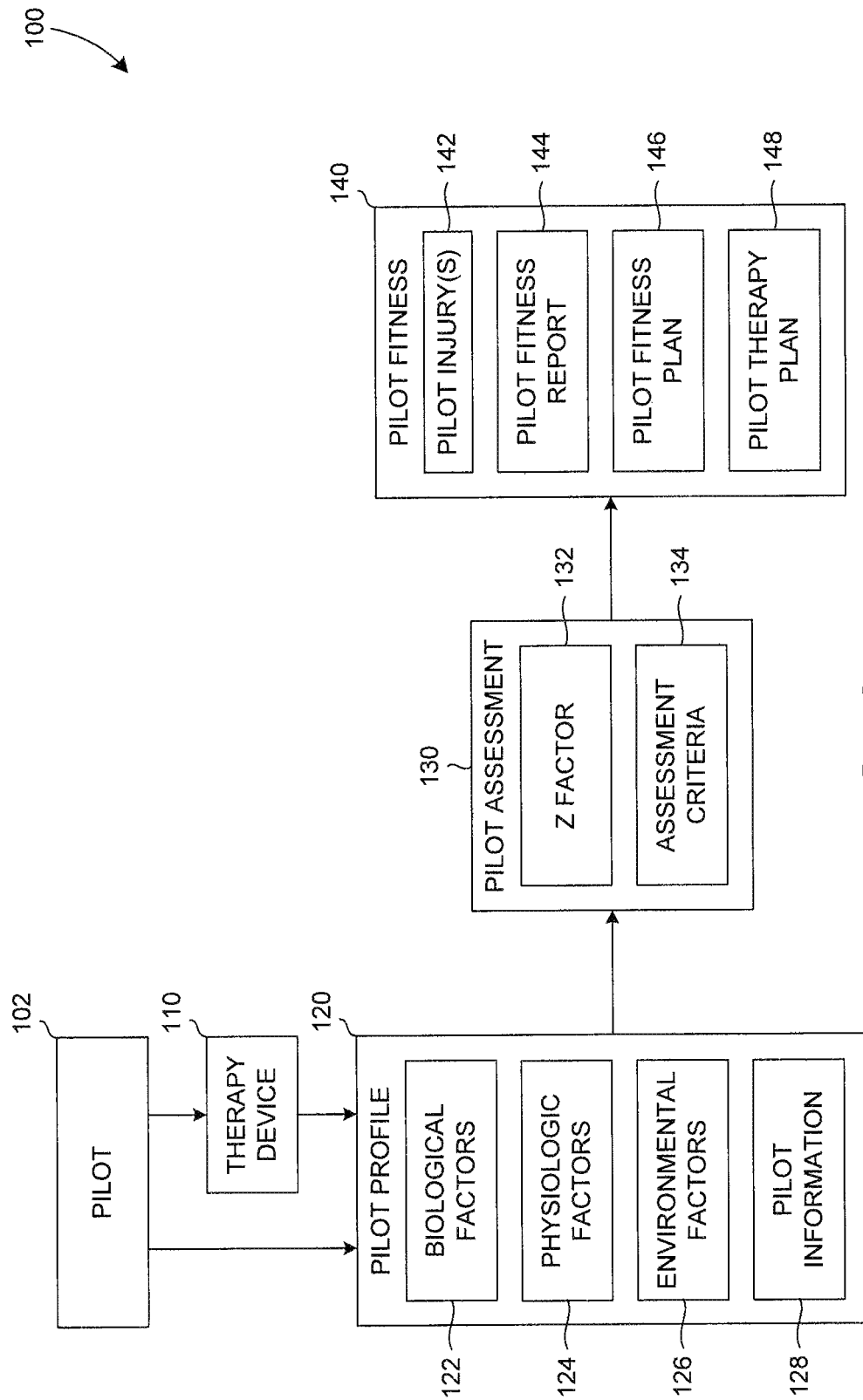
FIG. 1 illustrates an example pilot fitness system.

FIG. 1 illustrates an example pilot fitness system 100. The pilot fitness system 100 quantifies and evaluates the fitness of a pilot 102 using information regarding the pilot 102 and their current fitness performance using one or more therapy devices 110. A pilot's fitness can include their physical and mental state, which the pilot fitness system 100 can evaluate and/or quantify. For healthy pilots, fitness can include their suitability to perform their required duties, such as training and combat flight missions. The pilot fitness system 100 can assist the pilot in improving and/or maintaining their fitness for the rigors of their profession. For injured pilots, fitness can include assessing the extent of the injury and developing a rehabilitation plan to return the pilot to a suitable performance level. The pilot 102 interacts with the therapy device 110 to generate information regarding the pilot's 102 current fitness performance/state. Data provided by or about the pilot 102, including data from the therapy device 110 is collected as part of the pilot profile 120.

The pilot profile 120 contains information regarding the pilot 102, their fitness, duty and other information, classified in various categories. Such categories can include biological factors 122, physiologic factors 124, environmental factors 126 and other pilot information 128. The pilot profile 120, and information contained therein, can be used to quantify, evaluate and compare the fitness of the pilot 102. Pilot 102 fitness assessment can help to detect and evaluate injuries to the pilot 102, develop an injury treatment plan for the pilot 102, develop a fitness plan for the pilot 102 and other pilot 102 fitness related items. These plans and/or assessments can assist in maintaining a pilot 102 that is fit for duty and/or reduces pilot 102 downtime due to injury.

Information populating the various categories 122, 124, 126, 128 of the pilot profile 120 can be collected through a variety of methods and means. The information can be supplied by the pilot 102, through a pilot's 102 interactions with one or more therapy devices 110, or from other sources. The collected data can be organized into the various categories 122, 124, 126, 128 for use in assessments of the pilot 102 and their performance abilities. Each of the categories 122, 124, 126, 128, can require certain pilot 102 data that can be provided or acquired to perform one or more assessments 130 of the pilot 102.

The pilot assessment 130 can include a variety of different inputs, such as the Z factor 132 and various assessment criteria 134, that are used to develop the pilot assessment 130. The pilot assessment 130 can be a general assessment of the pilot 102 or a more specific assessment of the pilot 102 with respect to a duty, task, goal or other focused assessment narrower than general fitness of the pilot 102.

The Z factor 132 may be represented as one or more values (e.g., numerical values) that can be applied to one or more assessment criteria 134 to calculate a pilot fitness 140 for the pilot 102. The Z factor may be referred to as a biometric that identifies one or more aspects of a human subject, such as a pilot. The assessment criteria 134 can be selected to evaluate the overall fitness of the pilot 102 or selected to evaluate specific aspects of the pilot 102 fitness, such as in relation to one or more aspects of the pilot's 102 duty. The Z factor 132 value(s) reflects a relative importance or impact that aspects of the patient profile 120 have on pilot fitness 140 with respect to one or more assessment criteria 134.

A pilot fitness 140 can include pilot injury(s) 142, a pilot fitness report 144, a pilot fitness plan 146 and/or a pilot therapy plan 148. The pilot fitness 140 encompasses the physical and/or mental fitness state of the pilot, which can include medical records and pilot performance history. Pilot injury(s) 142 can include known and unknown injuries the pilot may have. For unknown injuries, the pilot fitness system 100, can assist in identifying the injury early so that measures can be taken to heal and/or minimize the impact of the injury(s) on the pilot. The pilot fitness report 144 can be generated by the pilot fitness system 100 and is an assessment of the pilot's current and/or historical fitness state. The fitness report 144 can include a mission readiness status of the pilot based on their fitness state. The fitness plan 146 can include a list of exercises and/or routines for the pilot to perform to improve and/or maintain their fitness. The fitness plan 146 can be developed and/or monitored by the pilot fitness system 100 to track improvement and/or decline in pilot fitness 140. The pilot therapy plan 148 can include mental and/or physical exercises and/or requirements for pilot injury 142 recovery. The therapy plan 148 can be generated and/or monitored by the pilot fitness system 100 to monitor the extent and healing of a pilot injury 142. The pilot fitness system 100 can compile the pilot fitness 140 in a report format for one or more of the pilot, their doctor, supervisor and/or other relevant party. The compiled report can contain all or a portion of the pilot fitness 140 information and can be customized or otherwise presented in a format suitable for the intended recipient.

Figure 2:
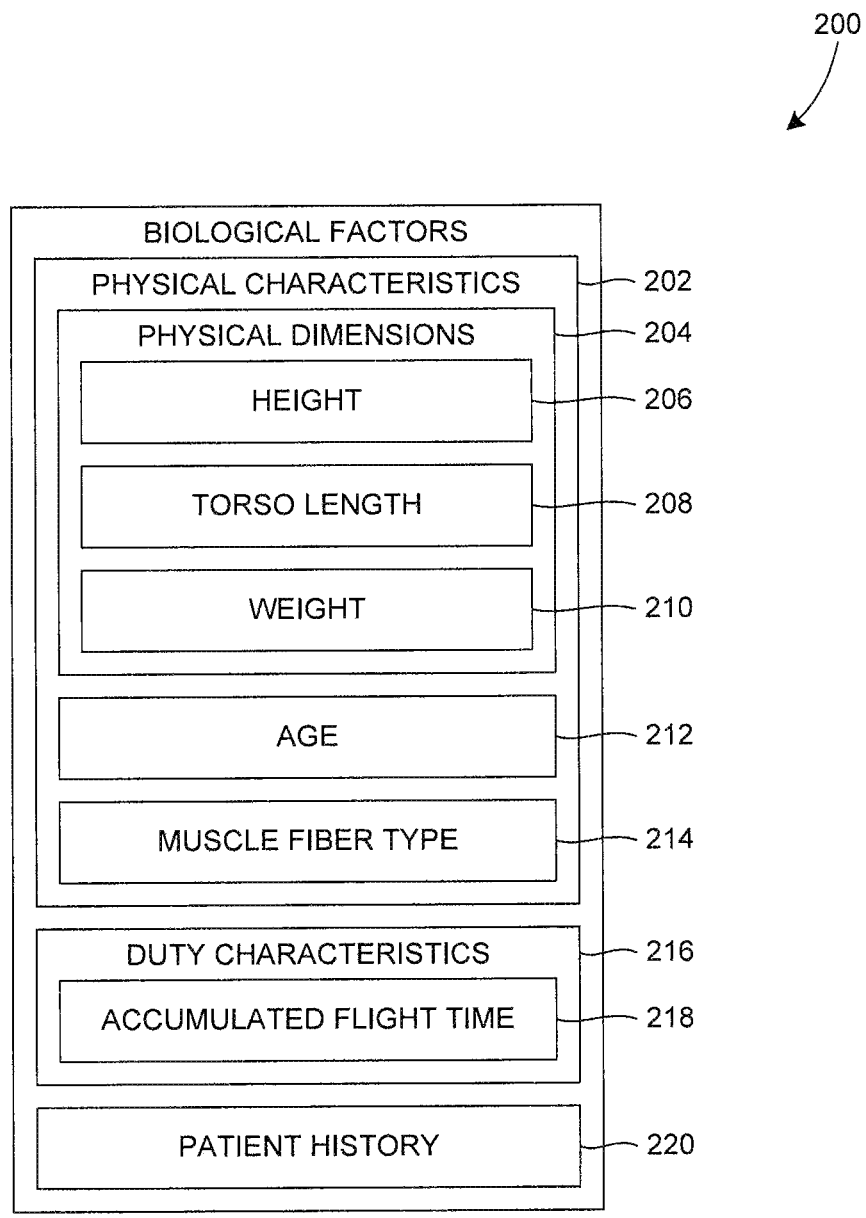
FIG. 2 illustrates example biological factors of an example pilot fitness system.

FIG. 2 is a block diagram of example biological factors 200, such as may be included in the pilot profile 120 of FIG. 1. The biological factors 200 are data and information regarding a pilot's inherent physical characteristics 202, the pilot's duty characteristics 216, and patient history 220. The physical characteristics 202 are likely to remain unchanged, minimally change or change in a known matter, over time. These are characteristics that a pilot cannot modify through exercise and/or a training regimen. The duty characteristics 216 are characteristics regarding the pilot's experience thus far. Data regarding the biological factors 200 of a pilot can be acquired using multiple methods and/or sources, such as through a survey completed by the pilot and minimally invasive/exertive measuring/testing.

Example physical characteristics 202 can include physical dimensions 204 of the pilot, age 212 of the pilot and muscle fiber type 214. The physical dimensions 204 of the pilot can be further broken down, as shown in the example of FIG. 2, and can include a height 206, a torso length 208 and weight 210 of the pilot. Additional physical dimensions 204 can be included and/or collected as needed for assessment of the pilot. Data regarding the physical dimensions of the pilot can be acquired through measurement, such as measuring the height 206 of the pilot and weighing the pilot on a scale to obtain a weight 210. Along with the pilot's age 212, other biological factor 200 data can be collected through a survey completed by a pilot.

A pilot's muscle fiber type 214 can include data regarding the pilot's muscle compositions, such as a ratio of slow twitch to fast twitch muscle tissue. The relative composition of the pilot's muscle tissue is likely to exhibit minimal to no change over time, hence the inclusion of muscle fiber type 214 as a biological factor 200. Aspects of a pilot's ability to perform one or more duties can be affected by the relative composition of the pilot's muscle tissues. A training or fitness program can assist the pilot with developing suitable fitness to overcome or lessen the impact of the individual pilot's muscle fiber type 214 composition with respect to their pilot duties.

Duty characteristics 216 can include information and/or data regarding the pilot's previous duty experience, such as the pilot's accumulated flight time 218. A pilot's duty experience can have an effect on the pilot's fitness and an effect on their fitness to perform such duties in the future. Additional data regarding other duty characteristics 216 can be collected as necessary or desired. As an example, FIG. 13 describes an example method 1300 in which inertial sensors capture time-based inertial measurement data with respect to a human subject (e.g., a pilot) located on-board an aircraft for each of a plurality of on-board sessions of the human subject with one or more aircraft. This time-based inertial measurement data may be combined over the plurality of on-board sessions to obtain a time-based inertial measurement profile for the human subject, which represents an accumulation of acceleration events experienced by the human subject at a machine interface (e.g., an aircraft cockpit).

A pilot's patient history 220 can include medical records and reports pertaining to both the physical and mental health and/or fitness of the pilot. The provided information and/or data can be used for assessing a pilot's fitness. Additionally, the assessment of a pilot's fitness can be used to indicate improvement and/or healing from previous injuries or medical deficiencies.

Figure 3:
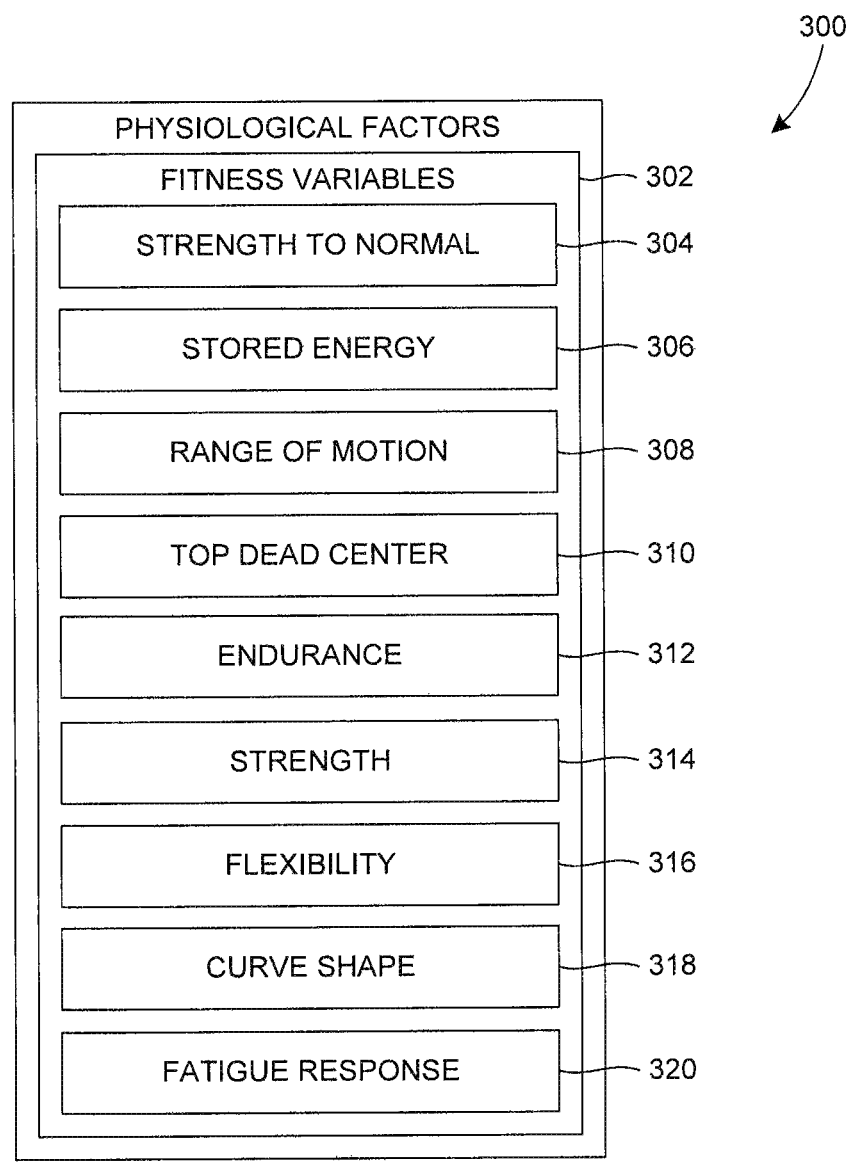
FIG. 3 illustrates example physiological factors of an example pilot fitness system.

FIG. 3 is a block diagram of example physiological factors 300, such as may be included in the pilot profile 120 of FIG. 1. Physiological factors 300 are measurable/quantifiable performance metrics of the pilot, such as fitness variables 302 and other factors/variables. The pilot can be tested using a variety of standardized methodologies and/or equipment (e.g., a physiological measurement device having range of motion sensors) to obtain data/information related to the pilot's physiological factors 300. The use of standardized methodologies and/or equipment assists with capturing or generating repeatable and verifiable data. Changes in the data over time can indicate trends associated with the measured physiological factor 300.

The fitness variables 302 are various testable and quantifiable fitness abilities of the pilot. One or more testing methodologies and/or test equipment can be used to evaluate and score the pilot's performance with regards to each of the fitness variables 302. The pilot can be tested broadly, such as tested in each of the example fitness variables 302 shown in FIG. 3, to assist with assessing a general or overall fitness of the pilot. Alternatively, the pilot testing can be limited to one or more selected fitness variables 302 based on the relation of the selected fitness variables 302 to the pilot fitness being assessed. While all fitness variables 302 can have an effect on a pilot's fitness, be it broad or specific, for a narrow focus of a pilot's fitness, the fitness variables 302 having the most effect on the pilot's narrow focused fitness can be selected for assessment and/or evaluation.

Example fitness variables 302 can include measurements and/or data regarding a pilot's strength to normal 304, stored energy 306, range of motion 308, top dead center 310, endurance 312, strength 314, flexibility 316, spinal curve shape 318 and fatigue response time 320, as well as combinations thereof. One or more testing methodologies, devices and/or equipment can be used to measure the pilot's performance with regards to the fitness variables 302.

Strength to normal 304 can be a comparison of the pilot's strength to a normal value. The strength to normal 304 fitness variable can be measured as an overall pilot strength or strength of a specific muscle group(s). This can be measured through quantifying the physical exertion of the pilot compared to a normal/expected value. Decreased strength compared to the normal value can indicate an injury causing a decrease in the expected strength of the pilot.

Stored energy 306 is a measure of the natural restorative force of the relaxed tissues of the patient. Stored energy 306 can skew a total strength measurement of the pilot since it adds to the efforts of the pilot's muscle exertions. The pilot can be positioned and/or manipulated to calculate the stored energy 306 of the pilot tissues in a flexed and/or compressed state. The stored energy 306 can be calculated for each of the strength measurements to be performed by the pilot. For example, the stored energy 306 of the pilot's torso tissue can be measured before the pilot's torso strength is measured. Subtracting the stored energy 306 from the measured strength value determines an actual muscular strength value of the pilot for the assessed area and/or muscle group(s).

Range of motion 308 can be measured in degrees and indicates an extent of movement of a joint. Each of the tested, or evaluated, joints of the pilot can have a previously evaluated range of motion and an associated normal or expected value. Comparison of the pilot's current range of motion of the joint with a previously measured range and the normal range can indicate the pilot's performance relative to their own historical and an expected amount. Additionally, pilot injuries can be assessed and/or discovered through range of motion 308 evaluations.

For example, a pilot with a minor injury or at an early stage of an injury without presenting symptoms, may not realize they are injured. The pilot may experience stiffness or soreness, which they may ignore or barely consider believing it to be minor and/or that the feeling will go away in a while. The stiffness or soreness can result in a reduced range of motion for joint effected by the injury, which can be detected and/or quantified during a range of motion 308 evaluation of the pilot. In this manner, pilot injury can be detected earlier so that preventative measures can be taken to minimize the impact of the injury and/or to assist with recovery from the injury, such as by modifying the duty of the pilot.

Top dead center 310 evaluations can assist with measuring a pilot's resting or normal body position. The pilot can sit on or in a device and be positioned so that the center of masses of the pilot's torso and head are aligned along a normal axis, i.e. perpendicular to a level axis. The pilot can then be asked to relax into their resting or normal body position and the difference between the top dead center 310 position and the pilot's normal body position can be measured, such as by a distance or angle. This measurement can be indicative of a pilot's natural tendency to hunch or slouch, which can have adverse effects on the pilot's spine. Additionally, the pilot's normal or resting position, such as the position they assume during performance of their duties, can magnify loading of the pilot's vertebrae and/or increase the risk of injury to the pilot during performance of their duties.

Endurance 312 is a measure of a pilot's physical stamina. A pilot's endurance 312 can be measured using a variety of different devices and/or methodologies and can be quantified in various measures or ratings. Additionally, a pilot's endurance 312 can be indicative of their muscle fiber composition, as slow-twitch muscles fibers are considered "endurance" muscle fibers. Further, the endurance 312 can be an overall evaluation of the pilot or for a specific muscle group(s) and/or physical action.

Strength 314 of a pilot is a measure of the ability of the pilot for physical exertion. This measurement can be an overall strength 314 measurement or a measurement of the strength 314 of one or more specific muscle groups of the pilot. Strength 314 of the pilot can be measured in a variety of ways, such as by measuring a pilot's exerted force using force sensors, counterweights and/or other strength 314 sensing devices/methodologies.

Flexibility 316 of a pilot is a measure of the range of movement of a joint or series of joints of the pilot and the lengths of muscles associated with the joint(s) of the pilot. Flexibility 316 can be indicative of joint resiliency, i.e. the ability of the joint(s) to flex and return to a normal position without injury to the joint(s). The flexibility 316 of the pilot can be measured using a variety of devices and/or methods, such as measuring extension or rotation of limbs about a joint(s) during stretching.

A curve shape 318 is the shape of graphs plotting fitness variables 302, such as the pilot's range of motion 308, strength 314, flexibility 316, and other graphs of other fitness variables 302. The curve shape 318 of these graphs can be used in evaluating and/or assessing the pilot's performance in the graphed fitness variable(s) 302. For example, a curve or graph of a pilot's range of motion 308, having a "dip" in performance at a certain angle of the joint can indicate an injury associated with that joint. Comparison of historical curve shapes 318 with the current curve shape of the fitness variable 302 can also indicate a pilot's increase or decrease in performance related to the fitness variable 302, such as based on the area under the historic curve compared to the area under the current curve.

A fatigue response 320 of the pilot is a fitness variable 302 that measures endurance performance of one or more muscle groups of the pilot. The one or more muscles groups of the pilot are isolated and the pilot performs a series of maximal effort exercises using the one or more muscle groups. The pilot is then allowed to rest for a period of time and then performs similar exercises at a reduced or variable exertion using the one or more muscle groups. The initial exertion effort is then compared with the later exertion effort to determine a pilot's fatigue response 320. Through training, a pilot's fatigue response 320 can be improved through general and/or targeted fitness or other programs.

Figure 4:
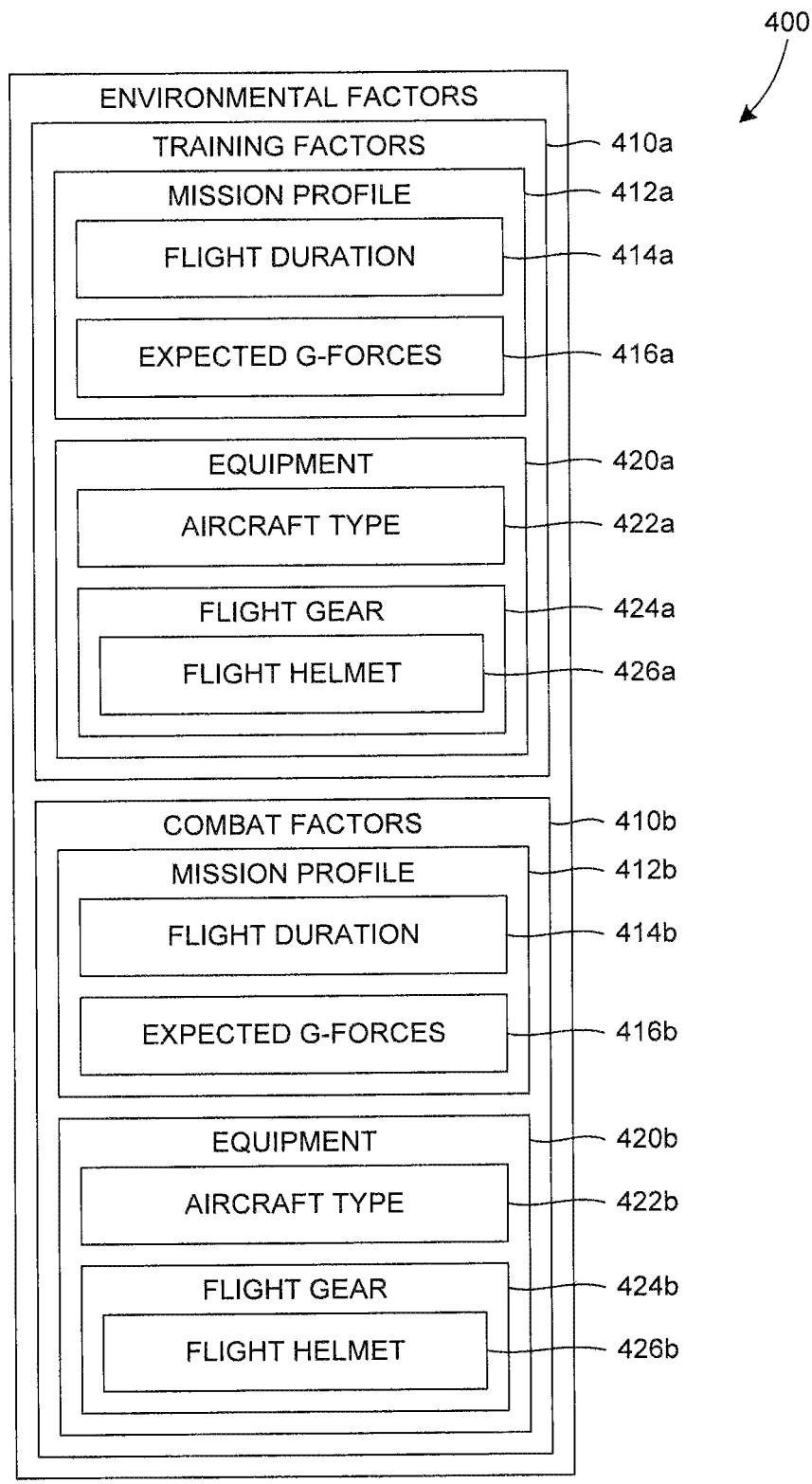
FIG. 4 illustrates example environmental factors of an example pilot fitness system.

FIG. 4 illustrates example environmental factors 400 of an example pilot fitness system. Environmental factors 400 are factors related to the pilot's specific duty and can include objective and/or subjective measures. The pilot's biological factors and physiological factors, can be evaluated in light of the pilot's environmental factors to determine a pilot's readiness and/or fitness to perform one or more aspects of their duty. Example environmental factors 400 can include training factors 410a and combat factors 410b. Since training missions are primarily for just that, training, the rigors a pilot is expected to undergo during such a mission can be preplanned and/or modified if necessary. Whereas, in combat, the situation is unplanned and the pilot is reactionary to the actions of the adversary and, therefore, the rigors a pilot may undergo during combat vary greatly in type and degree. Further, during training missions, a pilot may still be able to effectively participate in the training exercise with limited fitness deficiencies, such as minor injuries. During combat missions, due to the increased stress and the unknowns associated with the mission, it may be necessary or desired that the tolerable fitness deficiencies of the pilot be narrower than those associated with the training mission in order to maximize the likelihood of a favorable outcome of the combat mission.

Example training factors 410a can include a mission profile 412a and the pilot's equipment 420a. The mission profile 412a are the parameters regarding a mission, or flight, of the pilot, such as a flight duration 414a and expected g-forces 416a. During a flight, the pilot is limited in their ability to move which can have an effect on the fitness of the pilot, so the greater the flight duration 414a the more impact the time immobile can have on the fitness of the pilot. Additionally, during flight, g-forces can have an adverse effect on the pilot's fitness and, vice versa, the pilot's fitness can limit the g-forces the pilot can safely tolerate. Therefore, the expected g-forces 416a the pilot will undergo during the training mission can be considered for their effect on the pilot's fitness and/or the limitations the pilot's fitness will have on the expected g-forces 416a.

The equipment 420a of the pilot can include their aircraft type 422a and flight gear 424a, such as a flight helmet 426a. The aircraft type 422a has associated structural properties, such as a pilot seating position relative to controls, and performance properties, such as maneuverability, which can have an effect on the pilot's fitness and ability to perform their duties. The pilot's flight gear 424a, such as the flight helmet 426a, can also have an effect on the pilot's fitness and ability to perform their duties. For example, the flight helmet 426a can have a weight, and when maneuvering, the weight of the flight helmet 426a can strain the pilot's head, neck and/or spine, which can negatively impact the pilot's fitness by causing injury.

The combat factors 410b can be duplicative of the training factors 410a of the pilot but can have different values, weights, ranges and/or other characteristics different than similar training factors 410a. The combat factors 410b can include a mission profile 412b, such as a flight duration 412b and expected g-forces 416b, and equipment 420b, such as an aircraft type 422b and flight gear 424b including a flight helmet 426b. For combat missions, the combat factors 410b can be used to assess the pilot's ability to execute the combat mission.

Figure 5:
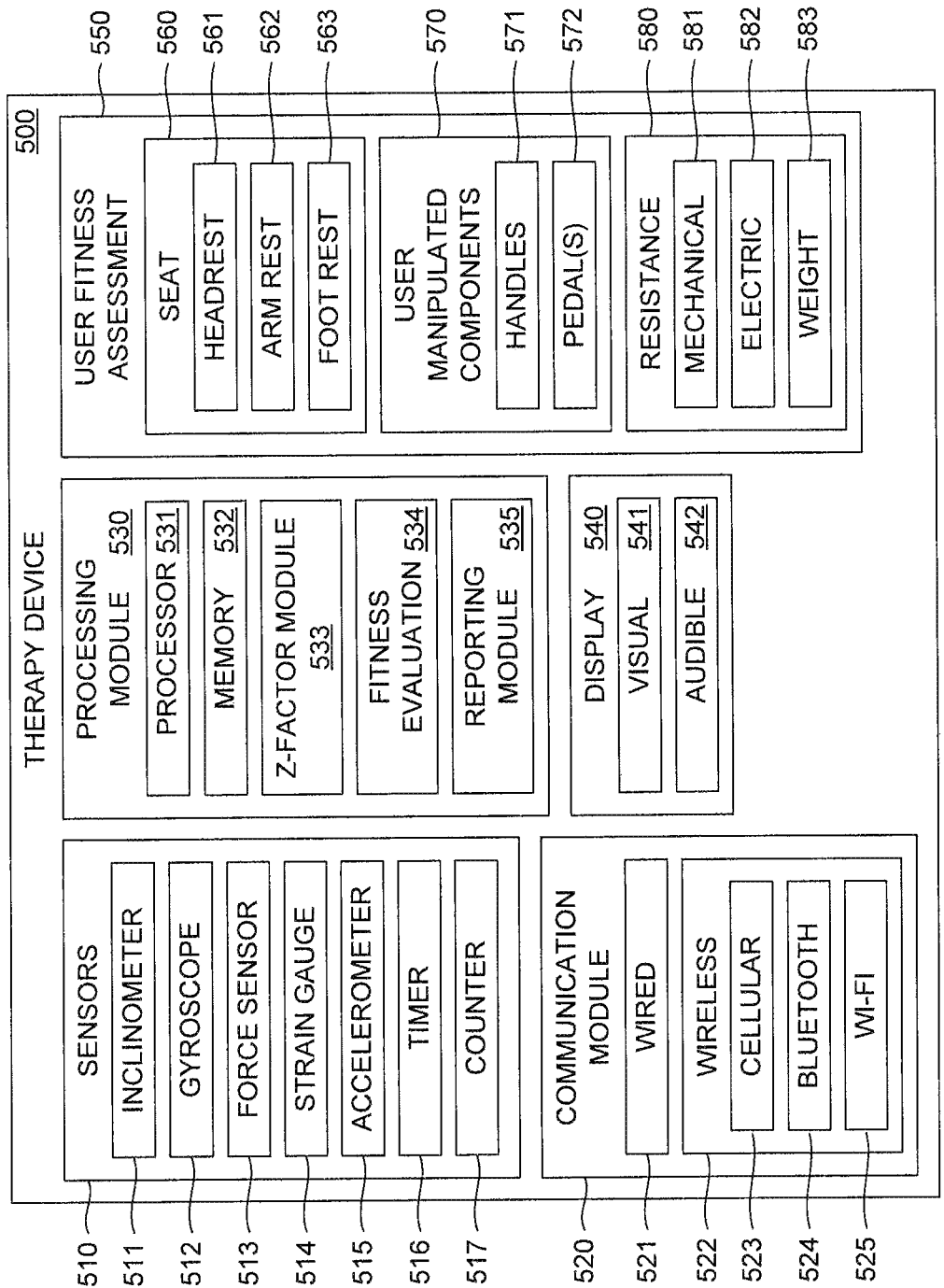
FIG. 5 illustrates an example therapy device of an example pilot fitness system.

FIG. 5 illustrates an example therapy device 500 of an example pilot fitness system. The pilot can interact with the therapy device 500 to capture various information and data regarding the pilot, such as the pilot's biological, physiological and/or environmental factors. The therapy device 500 can include a variety of components and/or modules, such as sensors 510, a communication module 520, processing module 530, a display 540, and a user fitness assessment 550. In addition to acquiring data regarding the pilot's fitness, the therapy device 500 can be used by the pilot as part of their fitness training and/or exercises.

The sensors 510 of the therapy device 500 can measure and/or quantify outputs, variables and/or other aspects of the pilot and their fitness. The interactions between the pilot and the therapy device 500 can be captured using one or more of the sensors 510 to collect the relevant data. Example sensors 510 can include an inclinometer 511, gyroscope 512, force sensor 513, strain gauge 514, accelerometer 515 (or other inertial sensor type), timer 516 and counter 517. Additional sensors can include an electrocardiograph, blood pressure sensor, range of motion sensor, thermometer and other patient physiological sensors. Each of the sensors 510 can be included in the therapy device 500 or otherwise connected thereto to allow data from the sensors 510 to be captured by the therapy device 500. The biological factors and/or physiological factors of the pilot can be measured, quantified, assessed and/or otherwise evaluated using the sensors 510 and therapy device 500.

The communication module 520 of the therapy device 500 can transmit information/data to and/or receive information/data from one or more external devices, systems and/or other sources. Communication between the therapy device and an external source can be done through a wired 521 connection of a wireless 522 connection using one or more communication methods/networks, such as a cellular 523 network, a Bluetooth® 524 network and/or a Wi-Fi 525 network. Data transmissions to and/or from the communication module 520 of the therapy device can be encrypted or otherwise protected to prevent interception of the communicated data.

The processing module 530 of the therapy device 500 can receive data collected from multiple sources to evaluate and/or develop a plan to improve the fitness of the pilot. The calculated fitness of the pilot, as evaluated by the processing module 530, can be used to determine the suitability of the pilot for performing required or requested duties. Additionally, the processing module 530 can develop the fitness plan specific to the individual pilot to improve the pilot's fitness in specific aspects and areas, such as to increase the pilot's ability to perform required duties and/or to minimize/prevent pilot injuries.

The processing module 530 can include a processor 531, memory 532, a Z factor module 533, a fitness evaluation 534 and a reporting module 535. The processor 531 and memory 532 can contain and/or execute the necessary processes to evaluate the pilot's fitness and other fitness related aspects, including a fitness plan for the pilot. The Z factor module 533 includes the processes and methodology for determining the one or more Z factors of the pilot for use in the fitness evaluation. Biological and physiological factors of the pilot are quantified, weighted and/or evaluated at the Z factor module to generate the Z factors for the pilot's fitness evaluation.

The fitness evaluation 534 is the application of the pilot's Z factors to the various environmental factors and/or other factors to determine the pilot's fitness. The pilot's fitness can be evaluated in a general or overall sense or can be more targeted, such as the pilot's fitness for performing specific tasks or duties. Additionally, the fitness evaluation 534 can calculate and/or determine a fitness improvement plan for the pilot. The fitness improvement plan can be targeted to address the fitness areas the pilot needs improvement in for better duty performance, injury prevention, and/or injury treatment.

The reporting module 535 can compile the fitness evaluation 534, including a fitness improvement plan, in a report for the pilot, therapist, doctor, commander and/or other interested party. The reporting module 535 can transmit the report to the communication module 520 and/or display 540 for transmission to the relevant party(s). The compiled report can be presented in a customized or standardized format for ease of interpretation of the data. Additionally, the report to one or more parties can be different that the report transmitted to another party. For example, a report compiled for the pilot can contain less technical language, more generalized statements and a fitness improvement plan. Whereas, a report compiled for the pilot's therapist and/or doctor can include more precise, technical language and statements and the fitness improvement plan. The fitness improvement plan can require approval by the therapist, doctor or other pilot supervisor before the fitness improvement plan is provided to the pilot. Additionally, the therapist, doctor or other pilot supervisor can be provided an opportunity to modify the proposed fitness improvement plan before the pilot receives it.

The therapy device 500 can also include data storage for fitness evaluations 534 and any included fitness plans. The therapy device 500 can recall the fitness plans and evaluations and update, modify or generate new fitness plans and evaluations based on newly received or acquired pilot data. Additionally, if the pilot uses the therapy device 500 for fitness and therapy exercises, the therapy device 500 can recall the individual's evaluation(s) and fitness plan(s) for monitoring and guidance during the pilot's fitness exercises.

The therapy device 500 can include the display 540 to relay information locally to a user of the device 500. The display 540 can include one or more of a visual 541 and/or audible 542 display. The visual 541 display can include light and/or screens to communicate information to the user. The audible 542 display can provide sound based output to communicate information to the user. The display 540 can also function as a user interface, such as a touchscreen visual 541 display or voice control audible 542 display.

The user fitness assessment 550 includes the components with which a user, such as the pilot, will interact with the therapy device 500 to generate and capture the data for use in evaluating their fitness. The user fitness assessment 550 can be connected to the sensors 510 to capture the user output through the user fitness assessment 550. Components of the user fitness assessment 550 can include a seat 560, user manipulated components 570 and resistance 580 that the user can interact with. These components may collectively be incorporated into a physiological testing device as described in further detail with reference to method 1300 of FIG. 13, for example.

The seat 560 can include a headrest 561, arm rest 562 and a foot rest 563. The user can sit in the seat 560 and positioned, such as using the headrest 561, arm rest 562 and foot rest 563, to acquire measurement of the user and/or position the user for fitness exercises/tests. The seat 560 can be adjusted so that the user is properly aligned for measuring and testing.

The user manipulated components 570 can include handles 571 and pedal(s) 572 that the user can interact with to generate fitness data. For example, a user can grip handles 571 to pull or push to generate data, such as exerting a force against resistance 580. Similarly, the pedal(s) 572 can be pushed or pulled by the user's feet and/or hands to generate data.

The resistance 580 can be connected to one or more of the user fitness assessment 550 components to assist in quantifying a user's effort. Various forms and systems of resistance 580 can be included, such as mechanical 581, electrical 582 and/or weight 583 resistance. Examples of mechanical 581 resistance can include springs, torsion bars and other forms of mechanical resistance. Electric 582 resistance can include a generator that is rotated in response to the user applied force. By varying the electrical demand on the generator, the resistance to movement by the user can be adjusted. Weight 583 resistance can be similar to a weight machine in which a weight is moved by a user input and the weight can be varied to alter the resistance to movement due to the user input.

Figure 6:
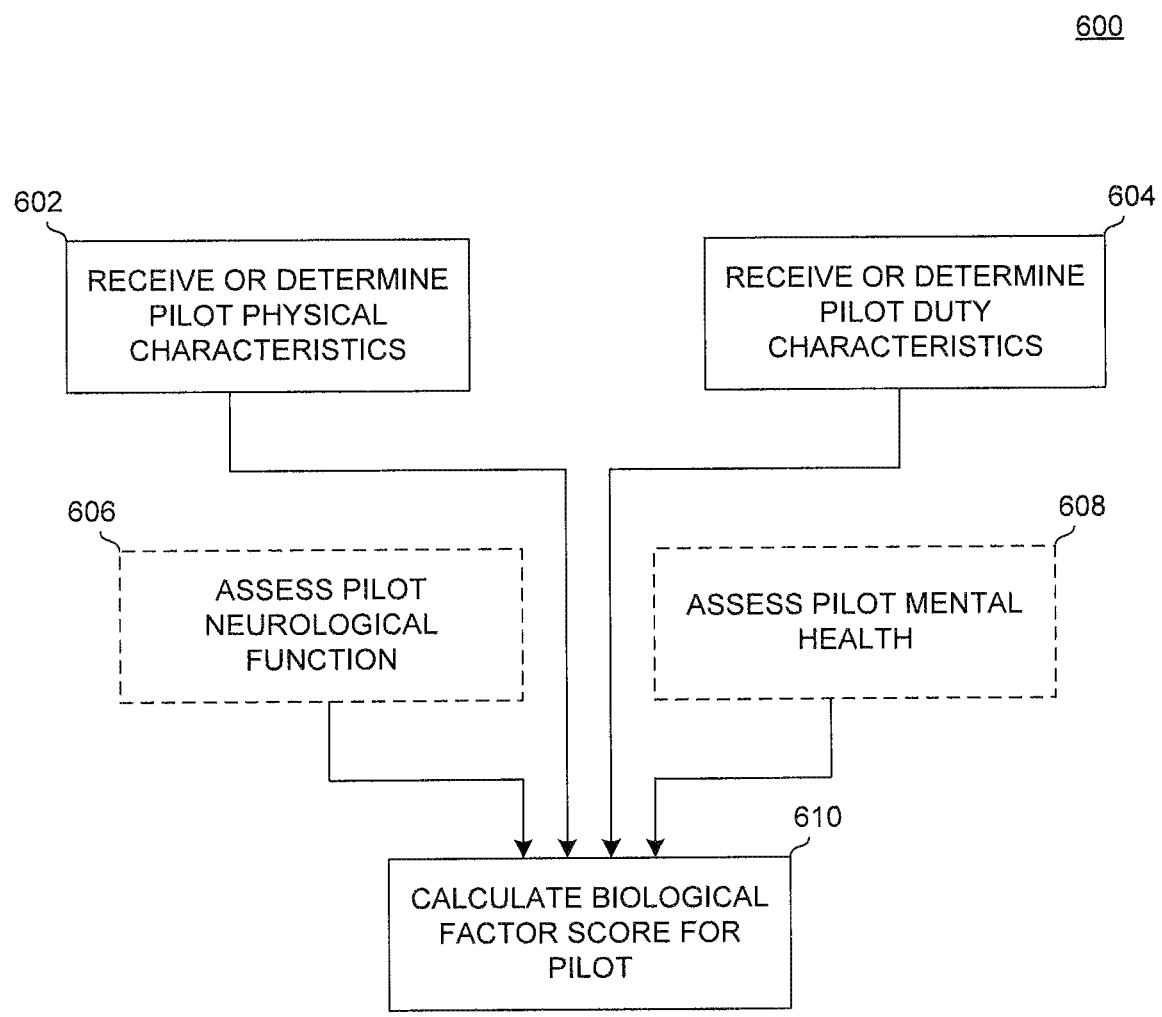
FIG. 6 illustrates an example process or method for calculating a biological factor score.

FIG. 6 is an example process, or method, 600 for calculating a biological factor score. Various data is collected and processed to determine the biological factor score for a pilot. Collected data can include receiving and/or determining pilot physical characteristics 602 and/or pilot duty characteristics 604. Optionally, an assessment of the pilot's neurological function 606 and mental health 608 can be included as part of the data used to calculate the pilot's biological factor. After the various data is collected the biological factor score of the pilot can be calculated 610. Calculating the biological factor score can include assigning values to the collected data and/or weighting that data based on the relative importance of the collected data. These numerical values can then be evaluated and/or used in an algorithm to generate one or more biological factor scores.

Figure 7:
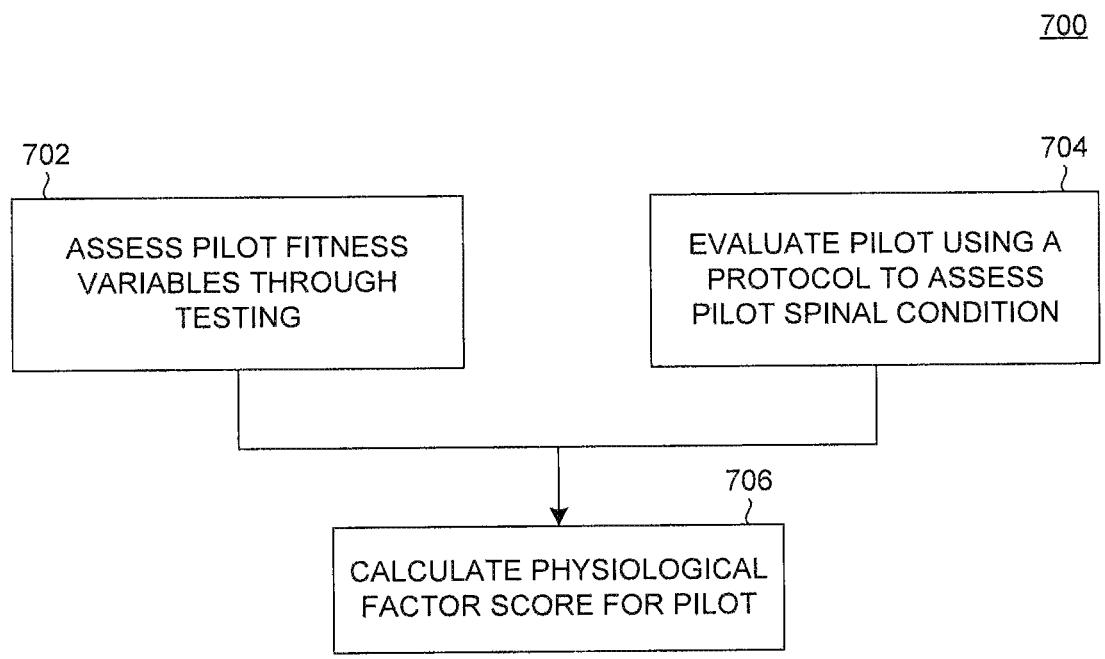
FIG. 7 illustrates an example process or method for calculating a physiological factor score.

FIG. 7 is an example process, or method, 700 for calculating a physiological factor score. Various data regarding fitness variables of the pilot is collected and used to calculate the physiological factor score. Collected data can include assessing the pilot's fitness variables through testing 702, such a through use of a therapy device, and an evaluation of the pilot's spinal condition using an assessment protocol 704. The collected data can then be used to calculate a physiological factor score for the pilot 706. The calculated physiological factor score can be a single value or can be a set of values, with each value corresponding to a specific fitness variable.

Figure 8:
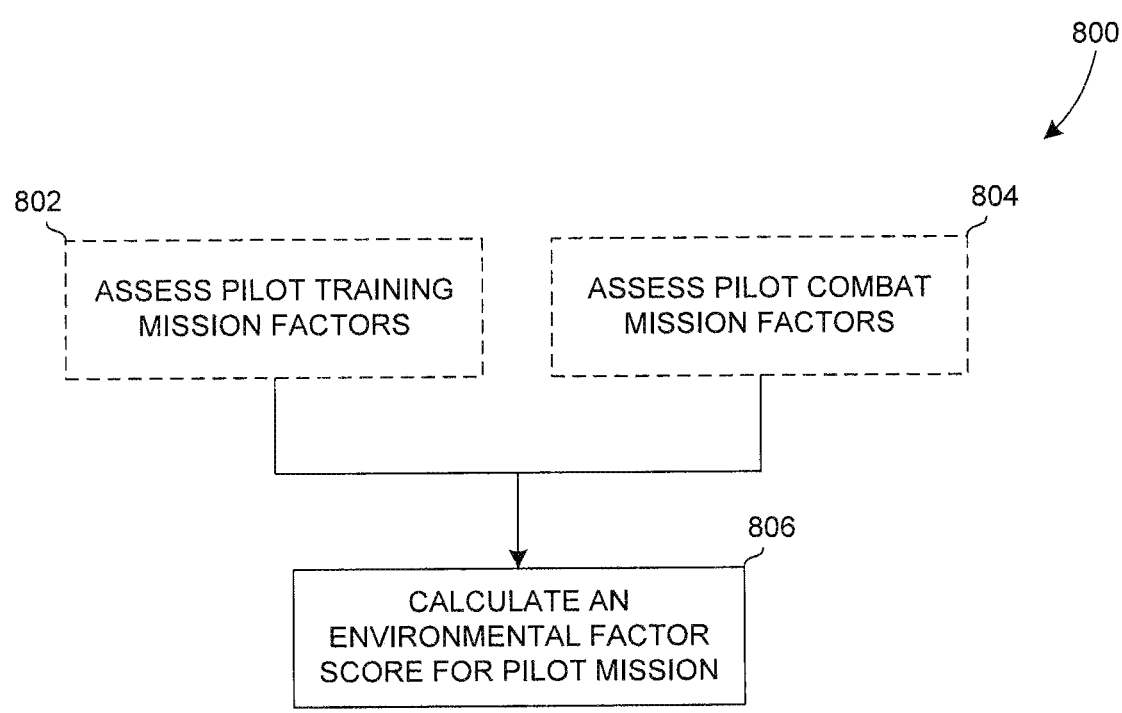
FIG. 8 illustrates an example process or method for calculating an environmental factor score.

FIG. 8 is an example process, or method, 800 for calculating an environmental factor score. Various data regarding environmental factors of the pilot is collected and used to calculate an overall and/or individual environmental factor scores. To calculate the environmental factor score, an assessment of the pilot training mission factors 802 and/or the pilot combat mission factors 804 can be used. The mission factors can include various physiologic effects the pilot can be expected to experience during the mission, such as an expected g-load which can load a pilot's spine by multiplying the weight of a pilot's helmet.

Figure 9:
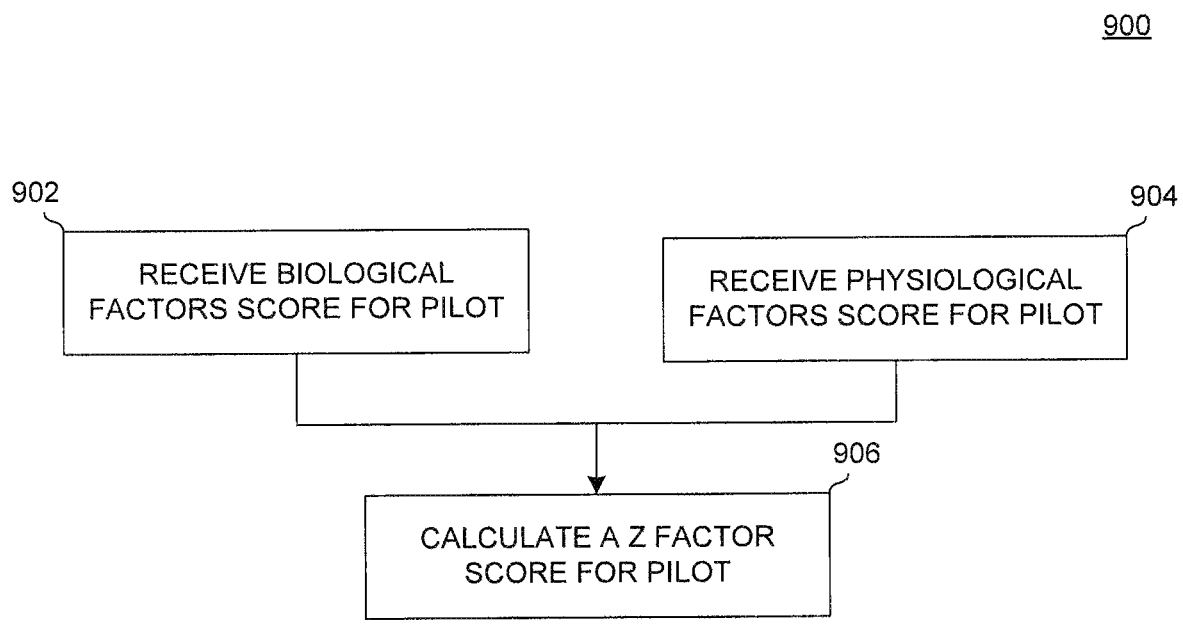
FIG. 9 illustrates an example process or method for calculating a Z factor score.

FIG. 9 is an example process, or method, 900 for calculating a Z factor score (Fz) for a pilot. A biological factors (Fb) score for the pilot are received at 902 and a physiological factor score (Fp) for the pilot is received at 904 and used to calculate a Z factor score for the pilot at 906. Regression analysis can be used for one or both of the biological factors and/or physiological factors to calculate expected values and/or determine an importance of the factor.

As part of the Z factor calculation, each fitness variable can be assigned an importance based on the relative effect the fitness variable has on the fitness assessment of the pilot. Additionally, or alternatively, the importance of the fitness variable can be determined based on regression analysis of one or more pilot assessments to determine relative impact the fitness variable has one the fitness of the pilot. For example, regression analysis can be used to determine that the range of motion fitness variable has less importance in a particular fitness assessment than the strength to normal fitness variable. The importance of the fitness variable can weight the fitness variable based on the effect the fitness variable has on the pilot fitness being assessed.

Additionally, the fitness variable performance of the pilot can be compared to a "normal" value that is the preferred or optimal performance level of the fitness variable for the pilot. Each fitness variable of the pilot can then be assigned a deficit score indicative of the pilot's performance relative to the "normal" value. The deficit score for each fitness variable can be used to further weight the importance of the fitness variable on the pilot fitness being assessed by highlighting the pilot's fitness deficiencies. To calculate the physiological factor score (Fp), the fitness variable importance (FVi) and deficit (FVd) can be multiplied, as an example.

The Z factor score can then be calculated by adding or otherwise combining the physiological factor score to the biological factor score. The biological factor score can be an individual biological factor score or an overall biological factor score, the biological factor score used in the calculation can be dependent on the fitness assessment being performed.

$$Fz = Fb + Fp \quad \text{(Eq. 1)}$$

$$Fp = FVi * FVd \quad \text{(Eq 2)}$$

Figure 10:
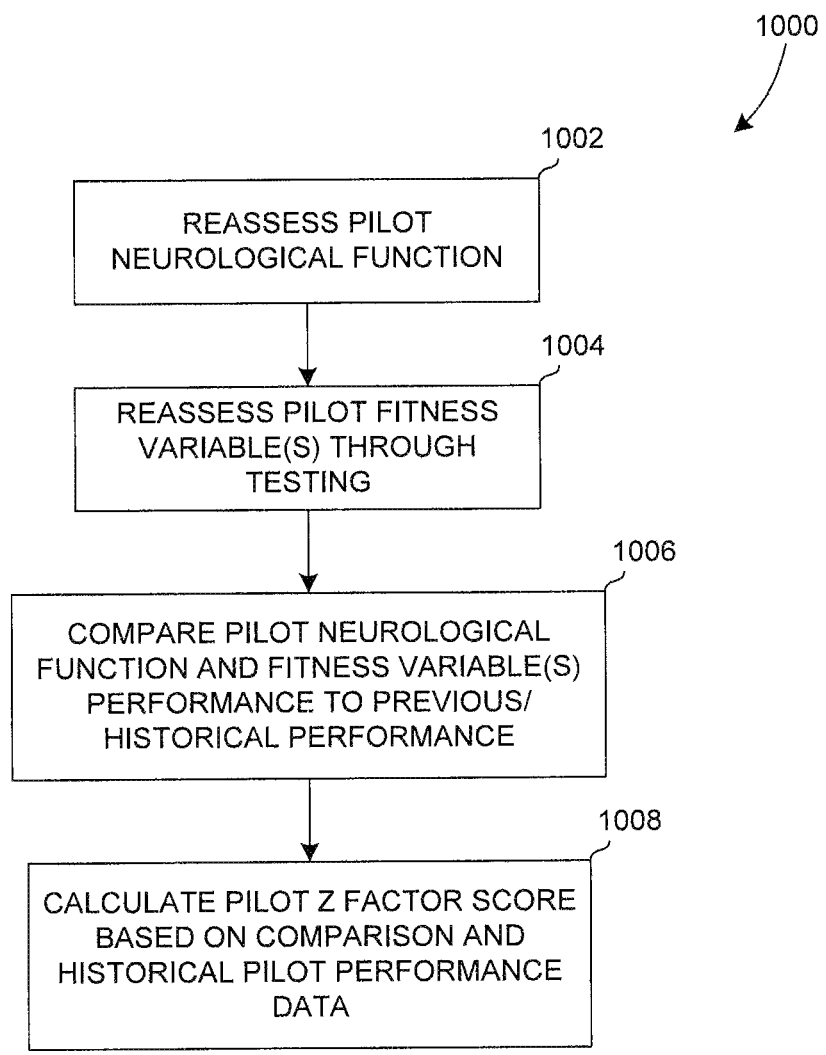
FIG. 10 illustrates a further example process or method for calculating a Z factor score.

FIG. 10 is a further example process, or method, 1000 for calculating a Z factor score of the pilot. At 1002 a pilot's neurological function is reassessed as are the pilot's fitness variable(s) at 1004. The reassessed pilot neurological function and fitness variable(s) are compared to previous and/or historical performance/values at 1006. This comparison allows for tracking of the pilot's fitness improvement or decline which can assist with identifying injuries and/or areas for fitness improvement. Using the comparison data, the pilot's Z factor score(s) can be calculated at 1008. The use of Z factor scores can standardize tracking of the pilot's fitness performance and provide a standard to facilitate comparison of one pilot to another pilot based on fitness performance. Z factors, biological factors, physiological and environmental factors allow for a standardized comparison of objective and/or subjective assessments of pilots and their fitness for duty.

Figure 11:
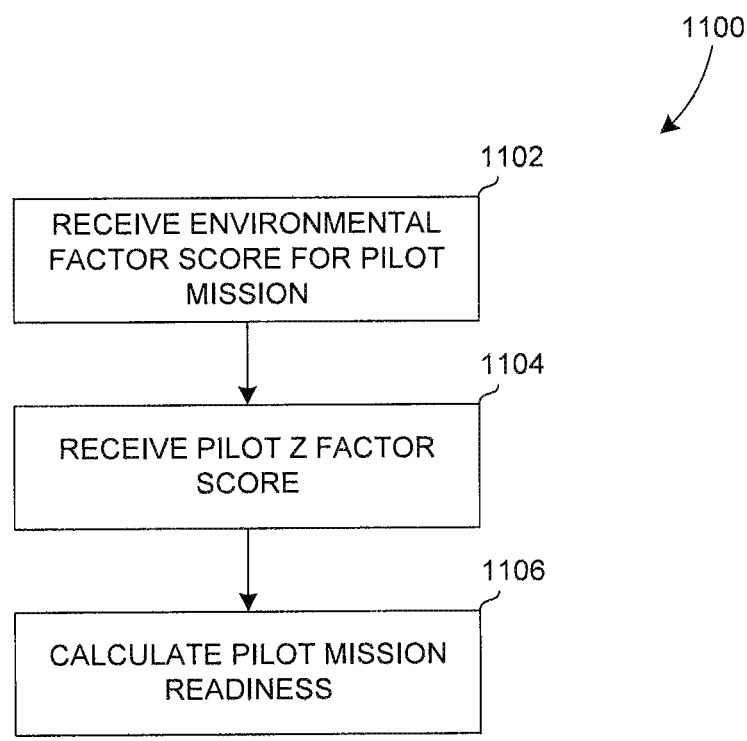
FIG. 11 illustrates an example process or method for calculating a pilot's mission readiness.

FIG. 11 is an example process, or method, 1100 for calculating a pilot's mission readiness. At 1102 an environmental factor score for the pilot's mission is received and at 1104 a Z factor score for the pilot is received. Using the Z factor score and environmental factor score, the pilot's mission readiness can be calculated at 1106. For example, the environmental factor score and Z factor score can be added to generate a mission readiness value for the pilot. Such assessment can be made on an individual environmental variable basis or can be an overall environmental variable group assessment. The mission readiness value for the pilot is a score indicative of the pilot's fitness suitability for the outlined mission. In this manner, a pilot can be selected or scrubbed from the mission based on their suitability to maximize mission success and/or minimize potential pilot injury.

Figure 12:
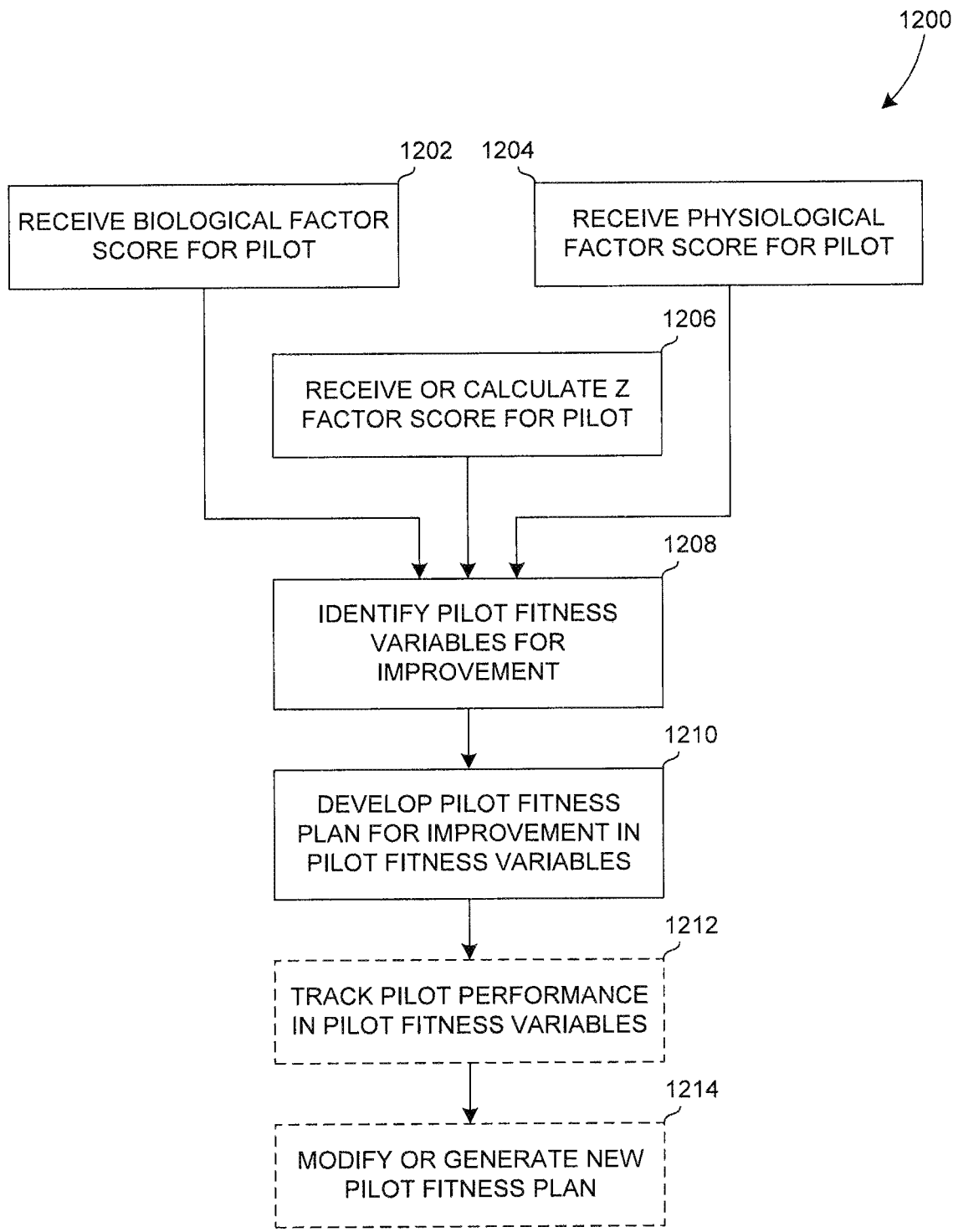
FIG. 12 illustrates an example process or method for developing a pilot fitness plan.

FIG. 12 is an example process, or method, 1200 for developing a pilot fitness plan and, optionally, tracking a pilot's performance during the plan and/or modifying the fitness plan in response to the pilot's performance. At 1202, 1204 and 1206 the various factors, biological factor score, physiological factor score, Z factor score, for the pilot are received and/or calculated. These factors and/or scores can be used to assess the current fitness state of the pilot. At 1208, fitness variables can be identified for improvement. The identification of fitness variables can be based on noted pilot fitness deficiencies, those fitness variables for which pilot improvement will have a larger effect, or other criteria. Based on the identified one or more fitness variables for improvement, a pilot fitness plan can be developed at 1210. The pilot fitness plan can include exercises, routines and/or other instructions for the pilot to follow to improve their performance in the identified fitness variables. At 1212, optionally, the pilot's performance with respect to the fitness variables can be tracked. By tracking pilot performance, improvement, or lack thereof, of the pilot in the fitness variable can be monitored. In response to this tracking, at 1214, optionally, the pilot fitness plan can be modified or a new fitness plan can be generated. If the tracking indicates a stall or slow improvement in the fitness variable, the pilot fitness plan can be modified to increase the improvement, such as through new exercises and/or modified exercise routine. Additionally, the tracking can indicate the pilot performance in one or more of the fitness variables has reached a suitable or optimal level and the pilot fitness plan can be modified to focus on improvement of a new or another fitness variable.

The various methods, such as those outlined in FIGS. 6-14 can be performed by or in conjunction with the example therapy device 500 of FIG. 5. The therapy device, alone or as part of system, can calculate the various factor scores and assessments. Additionally, the therapy device can generate, track and modify a pilot fitness plan. Further, one or more pilots can use the therapy device thus generating a wide range of data that can be processed by the therapy device for developing improvements in performance of the therapy device, such as through machine learning or other techniques. An example method 1400 incorporating machine learning is described in further detail with reference to FIG. 14.

Through machine learning, the therapy device 500 can identify trends, patterns and significant values in the collected user data, both individually and collectively. Using the trend and pattern analysis, the therapy device can better identify injuries and prepare more efficient rehabilitation plans. For example, if the therapy device 500 identifies a recurring injury in a population, the therapy device can advise exercises and/or fitness plans for the population that improve the user's fitness in order to prevent and/or minimize injury. Additionally, by tracking rehabilitation of multiple users suffering the same injury, the therapy device 500 can gather data regarding the injury treatment to better customize a treatment plan for a user that then suffers the same injury. The machine learning of the therapy device 500 can also be used to identify injury trends of a particular user and provide treatment and maintenance plans to minimize the recurrence of such an injury. Through machine learning, including collective user data, the therapy device 500 is more efficient at identifying injuries and better able to prepare customized fitness and treatment plans for users.

In an embodiment, the therapy device 500 can utilize machine learning to regularly reevaluate the various biological and physiological factor scores of a pilot and recalculate an accompanying Z factor score. For example, using the machine learning and the collected data, the therapy device 500 can adjust the importance score for one or more of the fitness variables. The therapy device 500 can detect a trend in the collected data indicating that a particular fitness variable has an increased impact or importance on the fitness of a user. Based on the trend data, the accompanying importance of the particular fitness variable can be increased to reflect this. Additionally, the therapy device can adjust the deficit scoring used as a part of the physiological factor score. Using machine learning, the therapy device 500 can adjust the "normal" value based on the collected data.

For example, the therapy device can use the machine learning and trend analysis to determine that users of a particular duty require an increased level of a fitness variable compared to the "normal" value of the fitness variable for the general public. For users with this particular duty, the therapy device 500 can automatically adjust the "normal" value of a fitness variable to reflect the increased optimum performance level of the users having the particular duty. The machine learning ability of the therapy device 500 can use not only the personal collected information of a particular user, but also the collected information of other users of the therapy device 500, to alter or otherwise modify the scoring and calculation of the biological, physiological, environmental and Z factors. The constant refinement of the data and calculations by the machine learning increase the effectiveness of the therapy device 500 in identifying injuries, performing fitness evaluations and calculating treatment and maintenance plans for the users.

Additionally, the machine learning capabilities of the fitness device 500 can allow for more detailed and nuanced analysis of the collected fitness data. This information can be compiled and used for a variety of ways to assist with user management decisions. For example, recurring injuries can be tracked and presented to a user manager to affect changes to assist with minimizing the injury recurrence. Additionally, such collective data can be compiled and analyzed using custom and/or particular criteria to allow for more efficient and effective user management decisions. In the case of pilots, the therapy device 500 can compile the collected data regarding the pilots and applying machine learning to identify a subset of the pilots based on desired management criteria, such as mission suitability. In this manner, the pilots most suitable for the particular mission can be selected in order to maximize mission effectiveness and success.

Figure 13:
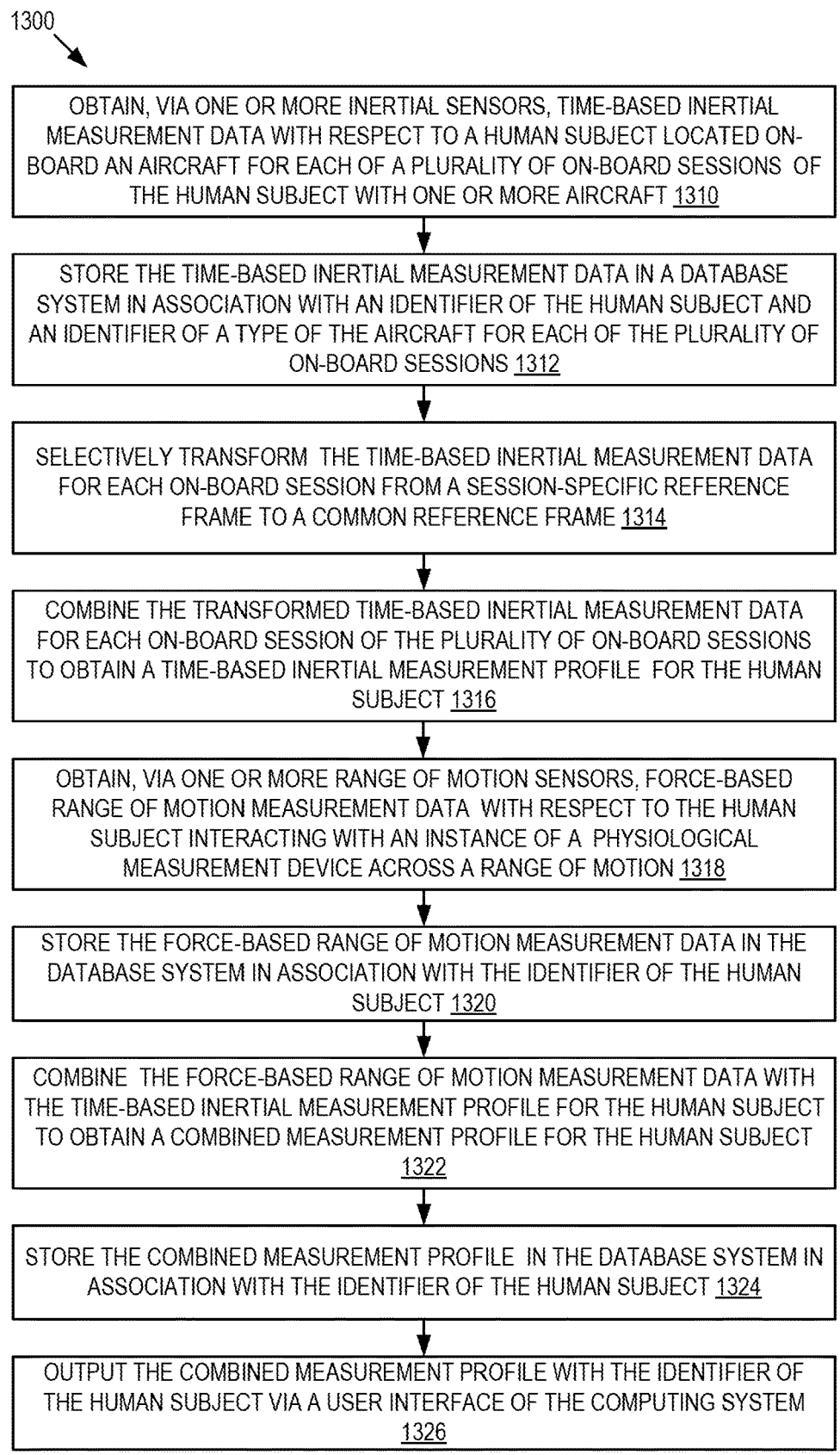
FIG. 13 is a flow diagram depicting an example method for sensor fusion of physiological and machine-interface factors as a biometric.
Figure 15:
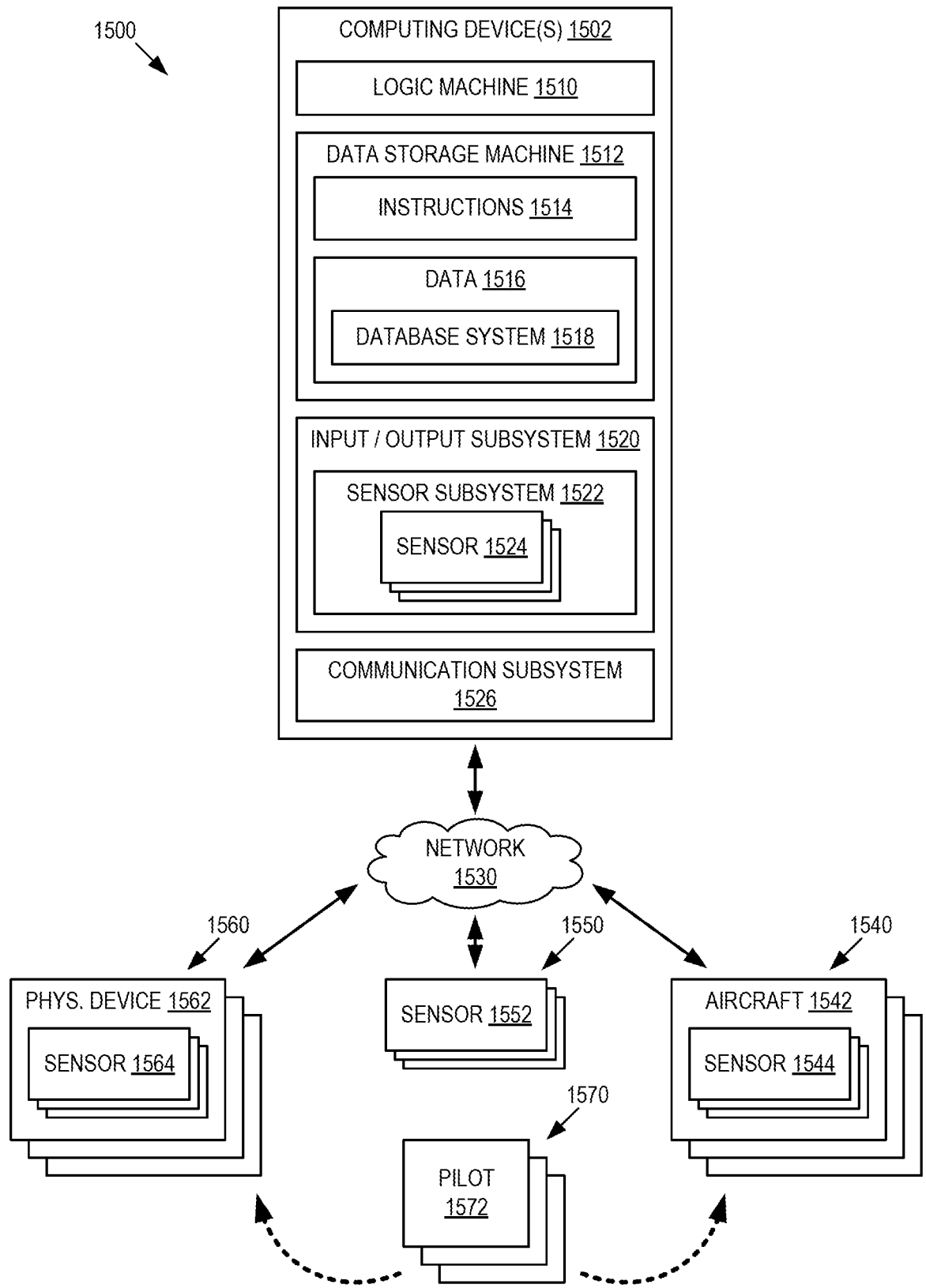
FIG. 15 is a schematic diagram depicting an example computing system.

FIG. 13 is a flow diagram depicting an example method 1300 for sensor fusion of physiological and machine-interface factors as a biometric. Method 1300 may be performed by a computing system implementing instructions that include a biometric assessment module, such as example computing system 1500 of FIG. 15. The biometric assessment module may include any of the modules previously described with reference to FIGS. 1-12 by which a Z factor may be determined. Within this context, the computing system through obtaining a biometric for a human subject may be referred to as a biometric computing system. Computing system 1500 of FIG. 15 is a non-limiting example of previously described therapy device 500 of FIG. 5 or a portion thereof.

At 1310, the method includes obtaining, via one or more inertial sensors, time-based inertial measurement data with respect to a human subject (e.g., a pilot) located on-board an aircraft for each of a plurality of on-board sessions of the human subject with one or more aircraft. An on-board session may refer to an individual flight conducted by the human subject on-board an aircraft. The human subject may engage in a plurality of on-board sessions involving numerous different aircraft over a period of time, such as tens, hundreds, or thousands of flights. In an example, each of the plurality of on-board sessions include flight time of the human subject on-board the aircraft. Additionally, each of the plurality of on-board sessions may further include seated time of the human subject on-board the aircraft, such as when the human subject is confined to a seat of a cockpit.

In an example, the one or more inertial sensors include one or more of an accelerometer, a gyroscope, an inclinometer, or other suitable type of inertial sensor. The one or more inertial sensors may include one or more multi-axis inertial sensors that each measure acceleration in multiple degrees of freedom that are included in the time-based inertial measurement data. In an example, at least one of the multi-axis inertial sensors measures acceleration in at least six degrees of freedom, including in three linear orthogonal dimensions (e.g., x, y, z coordinate axes) and in three rotational orthogonal dimensions (e.g., roll, pitch, yaw around x, y, z coordinate axes, respectively). In at least some implementations, the one or more inertial sensors include one or more wearable inertial sensors that are worn upon the human subject for each of the plurality of on-board sessions. For example, an inertial sensor may be mounted upon or incorporated into a helmet, a uniform, a wrist watch, etc. Alternatively or additionally, one or more of the inertial sensors may be located on-board and integrated with the aircraft for each of the plurality of on-board sessions.

At 1312, the method includes storing the time-based inertial measurement data in a database system of the biometric computing system in association with an identifier of the human subject and an identifier of a type of the aircraft for each of the plurality of on-board sessions. Each instance of time-based inertial measurement data corresponding to an on-board session may be associated with a time stamp, such as within metadata included in the data. The time-based inertial measurement data may provide a measure of acceleration magnitude and direction in up to six degrees of freedom at a periodic sampling frequency over the duration of the on-board session. As another example, inertial measurement data may indicate a maximum acceleration experienced by the human subject during an on-board session or a duration of time that acceleration exceeded a threshold during the on-board session.

At 1314, the method includes selectively transforming the time-based inertial measurement data for each on-board session from a session-specific reference frame in multi-dimensional space to a common reference frame in multi-dimensional space that is shared by the plurality of on-board sessions. For example, the transforming performed at 1314 may be used to align the time-based inertial measurement data across on-board sessions with respect to a common datum, which may include a feature of the human subject, a feature of the aircraft, the gravity vector, etc. In at least some implementations, each type of aircraft of the plurality of aircraft is associated with a respective aircraft profile that identifies an aspect of the transform from the time-based inertial measurement data for that aircraft to the transformed time-based inertial measurement data to the common reference frame for that aircraft. However, in other implementations, the transforming at 1314 may not performed or otherwise may be omitted. Transformed data at 1314 may also be stored in the database system in association with the identifier of the human subject, identifier of the aircraft, and time stamp of the on-board event.

At 1316, the method includes combining the transformed time-based inertial measurement data for each on-board session of the plurality of on-board sessions to obtain a time-based inertial measurement profile for the human subject. Multiple instances of time-based inertial measurement data may be combined in a variety of ways depending on implementation. In one example, more recent instances of time-based inertial measurement data may be weighted more heavily than less recent instances. Filtering of inertial measurement data may be performed based on thresholding (e.g., of acceleration, time, etc.) as part of the combining at 1316 to provide more relevant results. The combined time-based inertial measurement profile may be stored in the database system in association with the identifier of the human subject. The combined time-based inertial measurement profile may form part of the previously described duty characteristics 216 of FIG. 2, which forms a component of the biological factors.

In at least some implementations, method 1300 may further include periodically updating the time-based inertial measurement profile for the human subject as another instance of the time-based inertial measurement data is subsequently obtained for each additional on-board session. In an example, the more recently obtained instances of the time-based inertial measurement data may weighted more heavily than the less recently obtained instances of the time-based inertial measurement data within the time-based inertial measurement profile for the human subject, as may be identified by their respective time stamps.

At 1318, the method includes obtaining, via one or more range of motion sensors, force-based range of motion measurement data with respect to the human subject interacting with an instance of a physiological measurement device across a range of motion. This force-based range of motion measurement data may form some or all of the physiological factors previously described with reference to FIG. 3. In an example, the one or more range of motion sensors measure one or more of an angular range of motion and/or a linear range of motion included in the force-based range of motion measurement data. Additionally, the one or more range of motion sensors may further measure a magnitude of force exerted by the human subject across the range of motion. In at least some implementations, the one or more range of motion sensors generate the force-based range of motion measurement data responsive to the human subject exerting a force upon a moveable feature of the physiological measurement device across the range of motion. For example, the human subject may be asked to move a body part through a range of motion against a resistive force. The force-based range of motion measurement data may further include an activity identifier that identifies an activity performed by the human subject to generate the force-based range of motion measurement data. Respective instances of the force-based range of motion measurement data may be received for each of a plurality of activities performed by the human subject interacting with the instance of the physiological measurement device.

Figure 14:
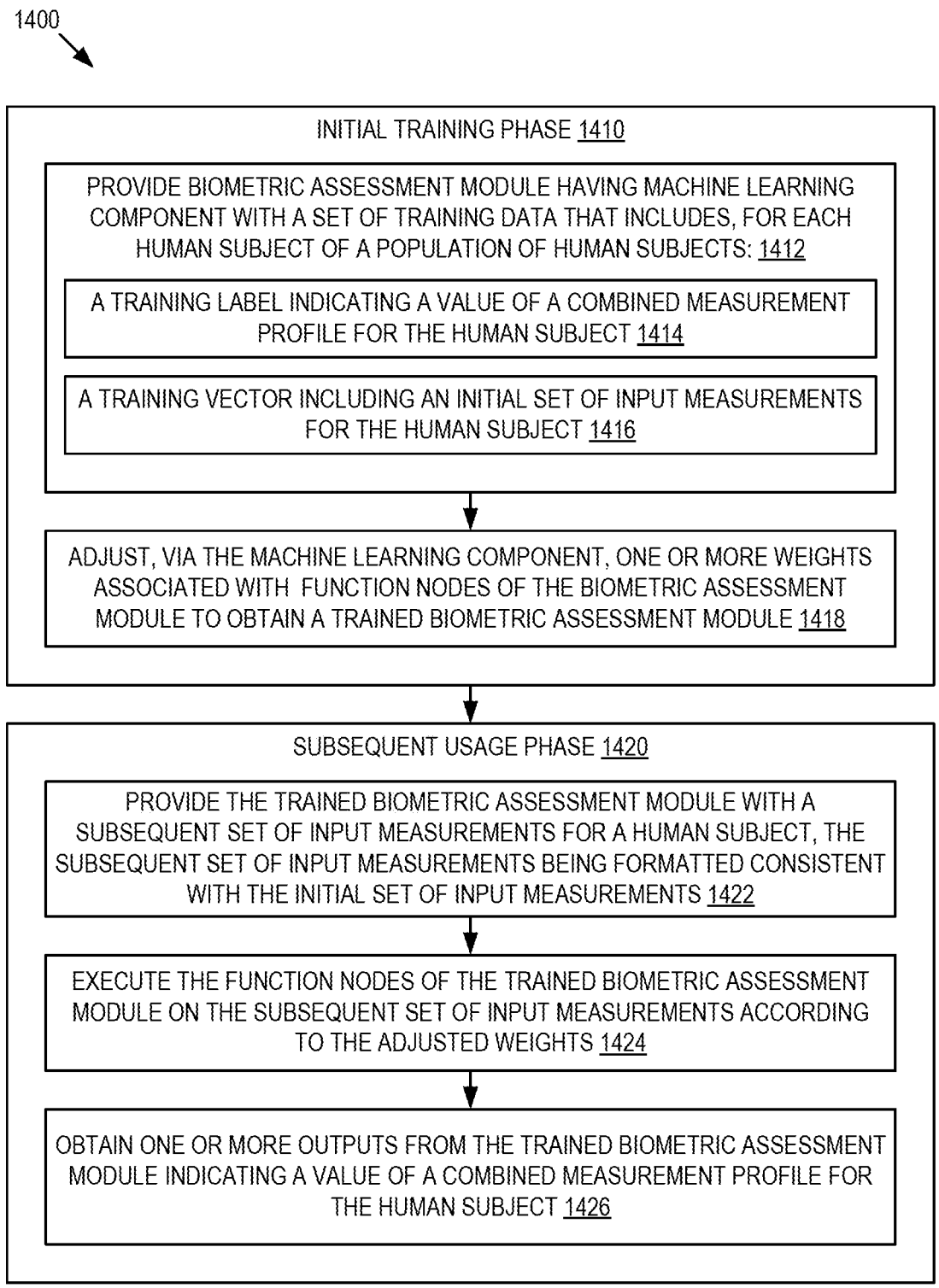
FIG. 14 is a flow diagram depicting an example method for training and using a biometric assessment module having a machine learning component to be implemented by a computing system.

While the phrase "range of motion" is used within the context of FIGS. 13-15, it should be understood that the disclosed range of motion sensors may be used to measure any of the physiological factors disclosed herein, including factors that rely on measurements of force exerted by a human subject or the ability of a human subject to maintain a particular position for a period of time or in resistance to an applied force without necessarily requiring movement of the human subject. For example, a range of motion sensor may detect a particular angle or linear positioning of a feature of a physiological measurement device at a particular instance in time, and can report that data as force-based range of motion measurement data.

At 1320, the method includes storing the force-based range of motion measurement data in the database system in association with the identifier of the human subject. This data may additionally be associated with a timestamp in the database system. The force-based range of motion measurement data may be periodically updated or replaced within the database system to reflect a more current state of the human subject.

At 1322, the method includes combining the force-based range of motion measurement data (or several instances thereof) with the time-based inertial measurement profile for the human subject to obtain a combined measurement profile for the human subject. This combined measurement profile may refer to the previously described Z factor, a portion thereof, or a precursor thereto. Accordingly, this combined measurement profile may be referred to as a biometric of the human subject that relies on sensor fusion. In an example, the force-based range of motion measurement data is combined with the time-based inertial measurement profile by applying one or more deterministic functions to obtain the combined measurement profile. The combined measurement profile may be periodically updated over time based on new measurement data by performing one or more of the preceding operations of method 1300.

In at least some implementations, machine learning may be applied to determining the combined measurement profile for a human subject. For example, the combined measurement profile may be obtained for the human subject by executing one or more function nodes of a biometric assessment module having a machine learning component that was previously trained by providing the biometric assessment module with a training label indicating a value of a combined measurement profile, and a training vector including an initial set of input measurements for each human subject of a training population of human subjects. Aspects of machine learning are described in further detail with reference to method 1400 of FIG. 14.

At 1324, the method includes storing the combined measurement profile in the database system in association with the identifier of the human subject.

At 1326, the method includes outputting the combined measurement profile with the identifier of the human subject via a user interface (e.g., graphical, audible, etc.) of the computing system.

In at least some implementations, method 1300 may further include comparing the combined measurement profile for the human subject to a normalized combined measurement profile of a population of other human subjects to obtain a differential value for the human subject, storing in the database system, and outputting the differential value for the human subject via the user interface.

FIG. 14 is a flow diagram depicting an example method 1400 for training and using a biometric assessment module having a machine learning component to be implemented by a computing system. In an example, the computing system may include computing system 1500 of FIG. 15.

The method may include an initial training phase 1410 during which operations 1412 and 1418 may be performed. At 1412, the method includes providing the biometric assessment module having the machine learning component with a set of training data. The training data may be used by the machine learning component to more accurately predict/output the combined measurement profile for a human subject in a subsequent usage phase given the training data as inputs. In an example, the training data includes, for each human subject of a population of human subjects used for training the system: (1) a training label 1414 indicating a value of a combined measurement profile for that human subject, and a training vector 1416 including an initial set of input measurements for that human subject.

The initial set of input measurements may include any of the factor inputs disclosed herein with respect to the Z factor and/or the combined measurement profile. In an example, the initial set of input measurements may include those measurements previously described with reference to method 1300 of FIG. 13. For example, the initial set of input measurements may include (1) force-based range of motion measurement data with respect to the human subject interacting with an instance of a physiological measurement device across a range of motion, and (2) time-based inertial measurement data with respect to the human subject located on-board an aircraft for each of a plurality of on-board sessions of the human subject with one or more aircraft.

At 1418, the method includes adjusting, via the machine learning component, one or more weights associated with function nodes of the biometric assessment module to obtain a trained biometric assessment module. The adjustment to the weights at 1418 improves a likelihood of accurately predicting/outputting the combined measurement profile for the human subject or other human subjects in a subsequent usage phase given the initial set of input measurements for that human subject. In an example, the machine learning component may include a deep neural network having a plurality of function nodes arranged at different layers of the network in which each function node includes at least one weight that may be adjusted during the training phase. However, other suitable machine learning models may be used.

The method may include a subsequent use phase 1420 during which operations 1422, 1424, and 1426 may be performed.

At 1422, the method includes providing the trained biometric assessment module with a subsequent set of input measurements for a human subject. In an example, the subsequent set of input measurements are formatted consistent with the initial set of input measurements, thereby enabling the biometric assessment module to apply its adjusted weights to achieve an accurate output in view of the previous training. Data may be referred to as being formatted consistent with training data even if, for example, a variable number of columns or rows for portions of the data can be variably sized. Continuing with the example used during the training phase, the subsequent set of input measurements may include (1) force-based range of motion measurement data with respect to the human subject interacting with an instance of the physiological measurement device across the range of motion; and (2) time-based inertial measurement data with respect to the human subject located on-board an aircraft for each of a plurality of on-board sessions of the human subject with the one or more aircraft of the initial set of input measurements. However, other suitable data inputs may be used, including any of the inputs disclosed herein.

At 1424, the method includes executing the function nodes of the trained biometric assessment module on the subsequent set of input measurements according to the adjusted weights to obtain one or more outputs from the trained biometric assessment module at 1426 indicating a value of a combined measurement profile for the human subject. As previously described, the combined measurement profile may include a plurality of values in some examples. As such, the trained biometric assessment module may output each of the plurality of values in these implementations.

In some embodiments, the methods and processes described herein may be tied to a computing system of one or more computing devices. In particular, such methods and processes may be implemented as a computer-application program or service, an application-programming interface (API), a library, and/or other computer-program product.

FIG. 15 schematically shows a non-limiting embodiment of a computing system 1500 that can enact one or more of the methods and processes described above. Computing system 1500 is shown in simplified form. Computing system 1500 may take the form of one or more computing devices 1502, which may include one or more personal computers, server computers, tablet computers, home-entertainment computers, network computing devices, gaming devices, mobile computing devices, mobile communication devices (e.g., smart phone), and/or other computing devices.

Computing system 1500 includes a logic machine 1510 and a data storage machine 1512. Computing system 1510 may further include an input/output subsystem 1520, a communication subsystem 1526, and/or other components not shown in FIG. 15.

Logic machine 1510 includes one or more physical logic devices configured to execute instructions. For example, the logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

The logic machine may include one or more processors (as an example of a logic device) configured to execute software instructions. Additionally or alternatively, the logic machine may include one or more hardware or firmware logic machines (as another example of a logic device) configured to execute hardware or firmware instructions. Processors of the logic machine may be single-core or multi-core, and the instructions executed thereon may be configured for sequential, parallel, and/or distributed processing. Individual components of the logic machine optionally may be distributed among two or more separate devices, which may be remotely located and/or configured for coordinated processing. Aspects of the logic machine may be virtualized and executed by remotely accessible, networked computing devices configured in a cloud-computing configuration.

Storage machine 1512 includes one or more physical storage devices configured to hold instructions 1514 executable by the logic machine to implement the methods and processes described herein. When such methods and processes are implemented, the state of storage machine 1512 may be transformed—e.g., to hold different data. Storage machine 1512 may further hold other forms of data 1516, which may be organized in a database system 1518, for example.

Storage machine 1512 may include removable and/or built-in devices. Storage machine 1512 may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. Storage machine 1512 may include volatile, nonvolatile, dynamic, static, read/write, read-only, random-access, sequential-access, location-addressable, file-addressable, and/or content-addressable devices.

It will be appreciated that storage machine 1512 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 1510 and storage machine 1512 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "module," "program," and "engine" may be used herein to describe an aspect of computing system 1500 implemented to perform a particular function. In some cases, a module, program, or engine may be instantiated via logic machine 1510 executing instructions 1514 held by storage machine 1512. It will be understood that different modules, programs, and/or engines may be instantiated from the same application, service, code block, object, library, routine, API, function, etc. Likewise, the same module, program, and/or engine may be instantiated by different applications, services, code blocks, objects, routines, APIs, functions, etc. The terms "module," "program," and "engine" may encompass individual or groups of executable files, data files, libraries, drivers, scripts, database records, etc. It will be appreciated that the term "service", may be used herein, to refer to one or more application programs executable across multiple user sessions. A service may be available to one or more system components, programs, and/or other services. In some implementations, a service may run on one or more server-computing devices.

Input/output subsystem 1520 may comprise or interface with one or more input devices and/or one or more output devices. Input devices may include user-input devices such as a keyboard, mouse, touch screen, game controller, microphone, camera, etc. Input devices may also include sensors of a sensor subsystem 1522, of which sensor 1524 is an example. Sensors of sensor subsystem 1522 may include the inertial sensors and range of motion sensors described with reference to method 1300 of FIG. 13, among other suitable sensor types. Sensors of sensor subsystem 1522 may also take the form of peripheral sensors, including sensors associated with a population of physiological training devices 1560, sensors associated with a population of aircraft 1540, and a population of wearable sensors 1550. For example, an instance of a physiological training device 1562 may include a range of motion sensor 1564, an instance of a particular type of aircraft 1542 may include an inertial sensor 1544, and a wearable sensor 1552 may include an inertial sensor. A population of human subjects 1570 (e.g., pilot 1572) may interact with one or more of the physiological training devices 1560, aircraft 1540, and/or wearable sensors 1550 to generate sensor data that may be transmitted to and/or received by computing devices 1502 via communications network 1530.

Output devices of input/output subsystem 1520 may include a graphical display, which may be used to present a visual representation of data held by the storage machine. This visual representation may take the form of a graphical user interface (GUI). As the herein described methods and processes change the data held by the storage machine, and thus transform the state of the storage machine, the state of the graphical display may likewise be transformed to visually represent changes in the underlying data. However, other suitable output devices may be used to provide a user interface by which a user may be presented data by the computing system. Input and/or output devices of input/output subsystem 1512 may be combined with logic machine 1510 and/or storage machine 1522 in a shared enclosure, or may be peripheral devices.

Communication subsystem 1526 may be configured to communicatively couple computing devices 1502 of computing system 1500 with one or more other computing devices. Communication subsystem 1526 may include wired and/or wireless communication devices compatible with one or more different communication protocols. As non-limiting examples, the communication subsystem may be configured for communication via a wired or wireless network (e.g., network 1530), including personal area network, local area network, and/or wide area network components. Communication subsystem 1526 may allow computing devices 1502 to send and/or receive messages to and/or from other devices via a network such as the Internet.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A biometric computing system, comprising:
a biometric sensor subsystem, including one or more inertial sensors and one or more range of motion sensors;
a logic machine including one or more logic devices; and
a data storage machine including one or more data storage devices having instructions stored thereon executable by the one or more logic devices of the logic machine to:
   obtain, via the one or more inertial sensors, time-based inertial measurement data with respect to a human subject located on-board an aircraft over a seated time during which the human subject is confined to a seat at a machine interface of the aircraft cockpit for each of a plurality of on-board sessions of the human subject with a plurality of aircraft;
   store the time-based inertial measurement data in a database system of the data storage subsystem in association with an identifier of the human subject and an identifier of a type of the aircraft for each of the plurality of on-board sessions;
   selectively transform the time-based inertial measurement data for each on-board session from a session-specific reference frame in multi-dimensional space to a common reference frame in multi-dimensional space that is shared by the plurality of on-board sessions, wherein each type of aircraft of the plurality of aircraft is associated with a respective aircraft profile in the data storage machine that identifies an aspect of the transform from the time-based inertial measurement data for that aircraft to transformed time-based inertial measurement data of the common reference frame for that aircraft;
   combine the transformed time-based inertial measurement data for each on-board session of the plurality of on-board sessions to obtain a time-based inertial measurement profile for the human subject which represents an accumulation of loading by acceleration events experienced by the human subject while confined to the seat at the machine interface of the aircraft cockpit;
   obtain, via the one or more range of motion sensors, force-based range of motion measurement data with respect to the human subject interacting with an instance of a physiological measurement device across a range of motion;
   store the force-based range of motion measurement data in the database system in association with the identifier of the human subject;
   combine the force-based range of motion measurement data with the time-based inertial measurement profile for the human subject to obtain a combined measurement profile for the human subject;
   store the combined measurement profile in the database system in association with the identifier of the human subject; and
   output the combined measurement profile with the identifier of the human subject via a user interface of the computing system.

2. The biometric computing system of claim 1, wherein the one or more inertial sensors include one or more of:
an accelerometer,
a gyroscope,
an inclinometer.

3. The biometric computing system of claim 1, wherein the one or more inertial sensors include at least one multi-axis inertial sensor that measures acceleration in at least six degrees of freedom included in the time-based inertial measurement data.

4. The biometric computing system of claim 1, wherein the one or more inertial sensors include at least one wearable inertial sensor that is worn upon the human subject for each of the plurality of on-board sessions.

5. The biometric computing system of claim 1, wherein the one or more inertial sensors include at least one inertial sensor located on-board and integrated with the aircraft for each of the plurality of on-board sessions.

6. The biometric computing system of claim 1, wherein the one or more range of motion sensors measure one or more of an angular range of motion and/or a linear range of motion included in the force-based range of motion measurement data.

7. The biometric computing system of claim 1, wherein the one or more range of motion sensors further measure a magnitude of force exerted by the human subject across the range of motion.

8. The biometric computing system of claim 1, wherein each of the plurality of on-board sessions include flight time of the human subject on-board the aircraft.

9. The biometric computing system of claim 1, wherein the instructions stored on the data storage machine are further executable by the logic machine to:
   periodically update the time-based inertial measurement profile for the human subject as another instance of the time-based inertial measurement data is subsequently obtained for each additional on-board session.

10. The biometric computing system of claim 9, wherein the more recently obtained instances of the time-based inertial measurement data are weighted more heavily than the less recently obtained instances of the time-based inertial measurement data within the time-based inertial measurement profile for the human subject.

11. The biometric computing system of claim 1, wherein the one or more range of motion sensors generate the force-based range of motion measurement data responsive to the human subject exerting a force upon a moveable feature of the physiological measurement device across the range of motion.

12. The biometric computing system of claim 11, wherein the force-based range of motion measurement data includes an activity identifier that identifies an activity performed by the human subject to generate the force-based range of motion measurement data.

13. The biometric computing system of claim 12, wherein respective instances of the force-based range of motion measurement data is received for each of a plurality of activities performed by the human subject interacting with the instance of the physiological measurement device; and
wherein the instructions stored on the data storage machine are further executable by the logic machine to:
combine each of the respective instances of the force-based range of motion measurement data with the time-based inertial measurement profile for the human subject to obtain the combined measurement profile for the human subject.

14. The biometric computing system of claim 1, wherein the force-based range of motion measurement data is combined with the time-based inertial measurement profile by applying one or more deterministic functions to obtain the combined measurement profile.

15. The biometric computing system of claim 1, wherein the instructions stored on the data storage machine are further executable by the logic machine to:
compare the combined measurement profile for the human subject to a normalized combined measurement profile of a population of other human subjects to obtain a differential value for the human subject; and
output the differential value for the human subject via the user interface.

16. The biometric computing system of claim 1, wherein the instructions stored on the data storage machine are further executable by the logic machine to:
combine the force-based range of motion measurement data with the time-based inertial measurement profile for the human subject to obtain the combined measurement profile for the human subject by:
executing one or more function nodes of a biometric assessment module having a machine learning component that was previously trained by providing the biometric assessment module with:
a training label indicating a value of a combined measurement profile, and a training vector including an initial set of input measurements for each human subject of a training population of human subjects.

17. A method performed by a biometric computing system, the method comprising:
obtaining, via one or more inertial sensors, time-based inertial measurement data with respect to a human subject located on-board an aircraft over a seated time during which the human subject is confined to a seat at a machine interface of the aircraft cockpit for each of a plurality of on-board sessions of the human subject with a plurality of aircraft;
storing the time-based inertial measurement data in a database system of the biometric computing system in association with an identifier of the human subject and an identifier of a type of the aircraft for each of the plurality of on-board sessions;
selectively transforming the time-based inertial measurement data for each on-board session from a session-specific reference frame in multi-dimensional space to a common reference frame in multi-dimensional space that is shared by the plurality of on-board sessions, wherein each type of aircraft of the plurality of aircraft is associated with a respective aircraft profile in a data storage machine that identifies an aspect of the transform from the time-based inertial measurement data for that aircraft to transformed time-based inertial measurement data of the common reference frame for that aircraft;
combining the transformed time-based inertial measurement data for each on-board session of the plurality of on-board sessions to obtain a time-based inertial measurement profile for the human subject which represents an accumulation of loading by acceleration events experienced by the human subject while confined to the seat at the machine interface of the aircraft cockpit;
obtaining, via one or more range of motion sensors, force-based range of motion measurement data with respect to the human subject interacting with an instance of a physiological measurement device across a range of motion;
storing the force-based range of motion measurement data in the database system in association with the identifier of the human subject;
combining the force-based range of motion measurement data with the time-based inertial measurement profile for the human subject to obtain a combined measurement profile for the human subject;
storing the combined measurement profile in the database system in association with the identifier of the human subject; and
outputting the combined measurement profile with the identifier of the human subject via a user interface of the computing system.

\* \* \* \* \*